United States Patent
Xu et al.

(10) Patent No.: US 10,874,621 B2
(45) Date of Patent: Dec. 29, 2020

(54) CATIONIC NANOPARTICLES FOR CO-DELIVERY OF NUCLEIC ACIDS AND THERAPEUTIC AGENTS

(71) Applicants: The Brigham and Women's Hospital, Inc., Boston, MA (US); Massachusetts Institute of Technology, Cambridge, MA (US)

(72) Inventors: Xiaoyang Xu, Cambridge, MA (US); Xueqing Zhang, Cambridge, MA (US); Omid C. Farokhzad, Waban, MA (US); Robert S. Langer, Cambridge, MA (US)

(73) Assignees: THE BRIGHAM AND WOMEN'S HOSPITAL, INC., Boston, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 15/029,084

(22) PCT Filed: Oct. 17, 2014

(86) PCT No.: PCT/US2014/061185
§ 371 (c)(1),
(2) Date: Apr. 13, 2016

(87) PCT Pub. No.: WO2015/058111
PCT Pub. Date: Apr. 23, 2015

(65) Prior Publication Data
US 2016/0243048 A1    Aug. 25, 2016

Related U.S. Application Data

(60) Provisional application No. 61/892,273, filed on Oct. 17, 2013.

(51) Int. Cl.
*A61K 31/713*    (2006.01)
*A61K 9/51*    (2006.01)
*A61K 33/24*    (2019.01)
*A61K 47/54*    (2017.01)
*A61K 49/00*    (2006.01)

(52) U.S. Cl.
CPC .......... *A61K 9/5153* (2013.01); *A61K 9/5192* (2013.01); *A61K 31/713* (2013.01); *A61K 33/24* (2013.01); *A61K 47/54* (2017.08); *A61K 49/0008* (2013.01)

(58) Field of Classification Search
None
See application file for complete search history.

(56) References Cited

FOREIGN PATENT DOCUMENTS

WO    2010005721    1/2010

OTHER PUBLICATIONS

Johnstone et al (The Effect of Ligand Lipophilicity on the Nanoparticle Encapsulation of Pt(IV) Prodrugs. Inorg. Chem., 2013, 52 (17), pp. 9915-9920).*
Dharmacon (http://www.seoulin.co.kr/shop/board/download.php?id=TechnicalDocument&no=160&div=0&PHPSESSID=b7bbd1ec0b3b174l0ba7f644e821a708 (2010)).*
Figueiredo et al (PLGA Nanoparticles for Ultrasound-Mediated Gene Delivery to Solid Tumors. Journal of Drug Delivery. vol. 2012, Article ID 767839, 20 pages) (Year: 2012).*
Bouclier, et al., "Physicochemical characteristics and preliminary in vivo biological evaluation of nanocapsules loaded with siRNA targeting estrogen receptor alpha", Biomolecules, 9(10):2881-90 (2008).
International Search Report for PCT,US2014/061185 dated Mar. 18, 2015.

* cited by examiner

*Primary Examiner* — Jake M Vu
(74) *Attorney, Agent, or Firm* — Pabst Patent Group LLP

(57) ABSTRACT

Nanoparticles containing an aqueous core containing one or more nucleic acids, such as siRNA, and a shell containing one or more hydrophobic cationic materials, one or more amphiphilic materials, and one or more therapeutic, diagnostic, and/or prophylactic agents are. The hydrophobic cationic material and the hydrophobic portion of the amphiphilic material provide a non-polar polymer matrix for loading non-polar drugs, protect and promoting siRNA molecule retention inside the NP core, and control drug release. The hydrophilic portion of the amphiphilic material can form a corona around the particle which prolongs circulation of the particles in the blood stream and decreases uptake by the RES.

15 Claims, 10 Drawing Sheets

Specification includes a Sequence Listing.

siRNA Dose

SEQUENCE LISTING

```
<160> NUMBER OF SEQ ID NOS: 14

<210> SEQ ID NO 1
<211> LENGTH: 9
<212> TYPE: PRT
<213> ORGANISM: Artificial Sequence
<220> FEATURE:
<223> OTHER INFORMATION: Plaque targeting peptide
<220> FEATURE:
<221> NAME/KEY: MISC_FEATURE
<222> LOCATION: (5)..(5)
<223> OTHER INFORMATION: Xaa = lysine or arginine
<220> FEATURE:
<221> NAME/KEY: MISC_FEATURE
<222> LOCATION: (8)..(8)
<223> OTHER INFORMATION: Xaa = aspartic acid or glutamic acid

<400> SEQUENCE: 1

Cys Arg Gly Asp Xaa Gly Pro Xaa Cys
1               5

<210> SEQ ID NO 2
<211> LENGTH: 9
<212> TYPE: PRT
<213> ORGANISM: Artificial Sequence
<220> FEATURE:
<223> OTHER INFORMATION: Plaque targeting peptide

<400> SEQUENCE: 2

Cys Lys Gly Gly Arg Ala Lys Asp Cys
1               5

<210> SEQ ID NO 3
<211> LENGTH: 19
<212> TYPE: RNA
<213> ORGANISM: Artificial Sequence
<220> FEATURE:
```

```
<223> OTHER INFORMATION: siRNA

<400> SEQUENCE: 3
cuuacgcuga guacuucga                                                    19

<210> SEQ ID NO 4
<211> LENGTH: 19
<212> TYPE: RNA
<213> ORGANISM: Artificial Sequence
<220> FEATURE:
<223> OTHER INFORMATION: siRNA

<400> SEQUENCE: 4
ucgaaguacu cagcguaag                                                    19

<210> SEQ ID NO 5
<211> LENGTH: 21
<212> TYPE: RNA
<213> ORGANISM: Artificial Sequence
<220> FEATURE:
<223> OTHER INFORMATION: siRNA

<400> SEQUENCE: 5
gcuguauaau gcauguugau a                                                 21

<210> SEQ ID NO 6
<211> LENGTH: 21
<212> TYPE: RNA
<213> ORGANISM: Artificial Sequence
<220> FEATURE:
<223> OTHER INFORMATION: siRNA

<400> SEQUENCE: 6
uaucaacaug cauuauacag c                                                 21

<210> SEQ ID NO 7
<211> LENGTH: 21
<212> TYPE: RNA
<213> ORGANISM: Artificial Sequence
<220> FEATURE:
<223> OTHER INFORMATION: siRNA

<400> SEQUENCE: 7
ucuucuugcu gguuggaaa g                                                  21

<210> SEQ ID NO 8
<211> LENGTH: 21
<212> TYPE: RNA
<213> ORGANISM: Artificial Sequence
<220> FEATURE:
<223> OTHER INFORMATION: siRNA

<400> SEQUENCE: 8
cuuuccaaac cagcaagaag a                                                 21

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
caatgacccc ttcattgacc                                                   20
```

```
<210> SEQ ID NO 10
<211> LENGTH: 20
<212> TYPE: DNA
<213> ORGANISM: Artificial Sequence
<220> FEATURE:
<223> OTHER INFORMATION: PCR Primer

<400> SEQUENCE: 10
gacaagcttc ccgttctcag                                               20

<210> SEQ ID NO 11
<211> LENGTH: 20
<212> TYPE: DNA
<213> ORGANISM: Artificial Sequence
<220> FEATURE:
<223> OTHER INFORMATION: PCR Primer

<400> SEQUENCE: 11
ttgtgatgaa gcgctggtag                                               20

<210> SEQ ID NO 12
<211> LENGTH: 20
<212> TYPE: DNA
<213> ORGANISM: Artificial Sequence
<220> FEATURE:
<223> OTHER INFORMATION: PCR Primer

<400> SEQUENCE: 12
agaggcagca catttcgtct                                               20

<210> SEQ ID NO 13
<211> LENGTH: 20
<212> TYPE: PRT
<213> ORGANISM: Artificial Sequence
<220> FEATURE:
<223> OTHER INFORMATION: PCR Primer

<400> SEQUENCE: 13

Thr Thr Thr Gly Thr Gly Cys Cys Ala Gly Cys Ala Ala Cys Ala Gly
1               5                   10                  15

Ala Ala Ala Gly
            20

<210> SEQ ID NO 14
<211> LENGTH: 20
<212> TYPE: DNA
<213> ORGANISM: Artificial Sequence
<220> FEATURE:
<223> OTHER INFORMATION: PCR Primer

<400> SEQUENCE: 14
ctgggatcca tcgctgtagt                                               20
```

CATIONIC NANOPARTICLES FOR CO-DELIVERY OF NUCLEIC ACIDS AND THERAPEUTIC AGENTS

CROSS REFERENCE TO RELATED APPLICATIONS

This application is a 371 application of the published International Application No. PCT/2014/061185, entitled "CATIONIC NANOPARTICLES FOR CO-DELIVERY OF NUCLEIC ACIDS AND THERAPEUTIC AGENTS", by Xiaoyang Xu, Xueqing Zhang, Omid C. Farokhzad and Robert S. Langer, filed Oct. 17, 2014, which claims the benefit of and priority to U.S. Ser. No. 61/892,273, filed Oct. 17, 2013, all of which are herein incorporated in their entirety by reference.

REFERENCE TO SEQUENCE LISTING

The Sequence Listing submitted on Oct. 17, 2014 as a text file named "BWH_21175_PCT_21_ST25.txt," created on Oct. 17, 2014, and having a size of 3,129 bytes is hereby incorporated by reference pursuant to 37 C.F.R. § 1.52(e)(5).

FIELD OF THE INVENTION

This invention is in the field of nanoparticles, particularly nanoparticles which can effectively co-deliver nucleic acids, such as siRNAs, and small molecule therapeutics.

BACKGROUND OF THE INVENTION

Advances in genomics and cell biology have highlighted the heterogeneity and complexity of cancer. It is generally accepted that cancer is usually the result of a combination of interconnected disease pathways that may not be treated effectively with one-dimensional therapeutic mechanisms. The inhibition of a pathway by single-drug therapy often results in the emergence of drug resistance and tumor relapse, largely because of pathway redundancy, cross-talk, compensatory and neutralizing actions, and anti-target activities that commonly occur with single-drug cancer therapy. In some cases, relapse can result in the emergence of phenotypically distinct and possibly more virulent tumors. For example, treatment of prostatic adenocarcinoma with androgen ablation therapies such as abiraterone or enzalutamide results in the development of abiraterone or enzalutamide refractory castration resistant prostate cancer (CRPC) that is phenotypically non-adenocarcinoma and represents a rare and often lethal form of prostate cancer with neuroendocrine phenotype.

Platinum agents are among the most widely used cytotoxic agents for cancer therapy. Cisplatin and other DNA adduct-forming chemotherapeutics cause DNA damage as their primary mechanism of cellular cytotoxicity. However, several cellular pathways are activated in response to their interaction with DNA, which include DNA repair pathways that remove the damage and human translesion synthesis (TLS) by specialized DNA polymerases that help the cells tolerate the DNA damage. The Rev1/Rev3L/Rev7-dependent error-prone TLS pathway has been shown to play an important role in cisplatin-induced mutations that improve the capacity of tumor cells to either repair or tolerate DNA damage, resulting in acquired chemoresistance. Recent studies using mouse lymphoma and lung cancer models have shown that the suppression of crucial gene products (Rev1 and Rev3L) involved in the error-prone TLS activity in mammalian cells can inhibit drug-induced mutagenesis so that relapsed tumors remain sensitive to subsequent treatment. It has been suggested that combining conventional chemotherapy with newly emerging siRNA therapeutics could be a promising strategy for improving the efficacy of chemotherapy through additive or synergistic effects.

Since the discovery of RNA interference (RNAi), synthetic siRNA has emerged as a class of attractive therapeutics for treatment of various diseases including cancer. Given the ability to target and silence nearly any gene of interest, specific siRNA can be constructed to target genes encoding proteins involved in DNA repair and the acquisition of multidrug resistance (MDR). Naked siRNA cannot readily cross cellular membranes due to its polyanionic and macromolecular characteristics, and it is susceptible to degradation by endogenous enzymes. Therefore, considerable efforts have been made to develop safe and effective vehicles in order to facilitate the delivery of siRNA into cells. Similarly, the methods by which chemotherapeutics are delivered also have a significant effect on the efficacy. Recent research has begun to explore the feasibility of combining chemotherapeutics with siRNA using a variety of nanocarrier platforms.

There remains a pressing need to engineer nanocarriers that are capable of delivering combination therapeutics involving siRNA since systemic delivery of siRNA remains challenging.

Therefore it is an object of the invention to provide nanocarriers, such as nanoparticles, which effectively co-deliver a combination of nucleic acids, such as siRNA, and small-molecule therapeutics, such as chemotherapeutic agents, and methods of making and using thereof.

SUMMARY OF THE INVENTION

Nanoparticles ("NP") containing an aqueous core containing one or more nucleic acids, such as siRNA, and a shell containing one or more hydrophobic cationic materials, one or more amphiphilic materials, and one or more therapeutic, diagnostic, and/or prophylactic agents have been developed. The hydrophobic cationic material and the hydrophobic portion of the amphiphilic material provide a non-polar polymer matrix for loading non-polar drugs, protect and promoting siRNA molecule retention inside the NP core, and control drug release. The hydrophilic portion of the amphiphilic material can form a corona around the particle which prolongs circulation of the particles in the blood stream and decreases uptake by the RES. Preferred siRNA molecules include those that inhibit the DNA repair pathways and human translesion synthesis (TLS) by specialized DNA polymerases that help the cells tolerate the DNA damage such as the Rev1/Rev3L/Rev7-dependent error-prone TLS pathway. These are preferably administered in combination with chemotherapeutic compounds such as ciplatin or other platinum derivatives.

DETAILED DESCRIPTION OF THE INVENTION

Figure 1A:
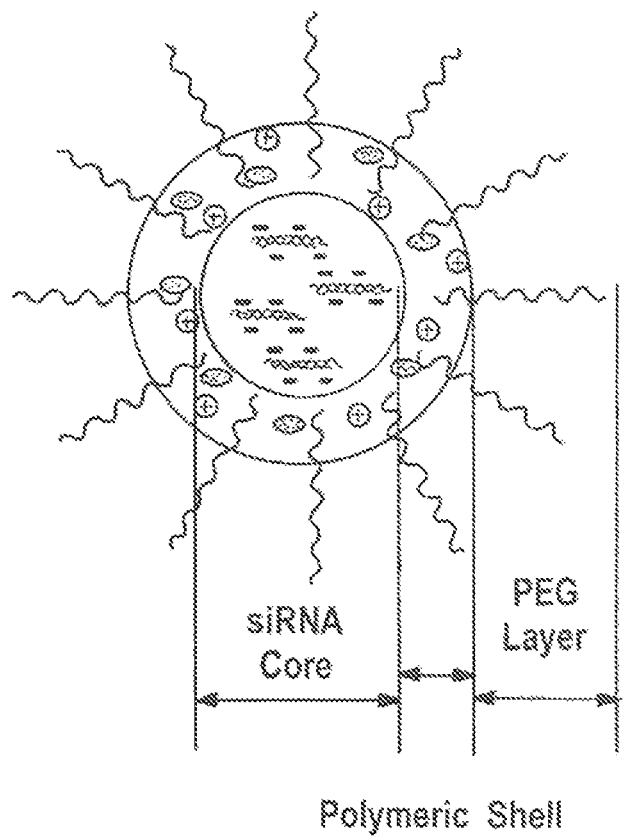
FIG. 1A is a schematic of PLGA-b-PEG/G0-C14 NPs. The particle contains three components: i) an outer PEG surface; ii) a PLGA/G0-C14 layer which plays two roles: a) carrying non-polar drugs in a polymer matrix and b) protecting and promoting siRNA molecule retention inside the NP core and controlling drug release; and iii) an aqueous inner core containing siRNA.

One of the earliest efforts utilizing this therapeutic method involved cancer treatment by targeted minicells containing specific siRNA followed by drug-loaded minicells, which efficiently reversed drug resistance in drug-resistant tumors and produced enhanced therapeutic efficacy in inhibiting tumor growth. However, to exert optimal effects, both the drug and siRNA may need to be temporally co-localized in the tumor cells. As a result, nanocarrier platforms that are capable of simultaneously delivering siRNA and anticancer drugs to the same tumor cells are a promising nanomedicine approach for improved cancer therapy.

I. Definitions

"Hydrophobic cationic material", as used herein, refers to a molecule containing a hydrophobic moiety covalently bound to a cationic moiety. The cationic moiety can contain a single cationic site (e.g., small molecule cationic moiety)

or a plurality of cationic sites (e.g., small molecule, oligomer, polymer, lipids, or dendrimer).

"Amphiphilic material" as used herein refers to a material containing a hydrophobic or more hydrophobic oligomer or polymer (e.g., biodegradable oligomer or polymer) and a hydrophilic or more hydrophilic oligomer or polymer.

"Oligomer", as used herein, generally refers to molecules having up to 10 repeat units.

"Polymer", as used herein, generally refers to molecules having more than 10 repeat units.

The terms "subject" or "patient", as used herein, refer to any organism to which the particles may be administered, e.g. for experimental, therapeutic, diagnostic, and/or prophylactic purposes. Typical subjects include animals (e.g., mammals such as mice, rats, rabbits, non-human primates, and humans) and/or plants.

The terms "treating" or "preventing", as used herein, can include preventing or alleviating one or more symptoms of a disease, disorder or condition from occurring in an animal which may be predisposed to the disease, disorder and/or condition but has not yet been diagnosed as having it; inhibiting one or more symptoms of the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

The terms "bioactive agent" and "active agent", as used interchangeably herein, include, without limitation, physiologically or pharmacologically active substances that act locally or systemically in the body. A bioactive agent is a substance used for the treatment (e.g., therapeutic agent), prevention (e.g., prophylactic agent), diagnosis (e.g., diagnostic agent), cure or mitigation of disease or illness, a substance which affects the structure or function of the body, or pro-drugs, which become biologically active or more active after they have been placed in a predetermined physiological environment.

The terms "sufficient" and "effective", as used interchangeably herein, refer to an amount (e.g. mass, volume, dosage, concentration, and/or time period) needed to achieve one or more desired result(s). The term "therapeutically effective amount" as used herein refers to that amount of the compound being administered which will relieve to some extent one or more of the symptoms of the disorder being treated.

The term "biocompatible", as used herein, refers to a material that along with any metabolites or degradation products thereof that are generally non-toxic to the recipient and do not cause any significant adverse effects to the recipient. Generally speaking, biocompatible materials are materials which do not elicit a significant inflammatory or immune response when administered to a patient.

The term "pharmaceutically acceptable", as used herein, refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration. A "pharmaceutically acceptable carrier", as used herein, refers to all components of a pharmaceutical formulation which facilitate the delivery of the composition in vivo.

A "pharmaceutical composition" refers to a mixture of one or more of the compounds, or pharmaceutically acceptable salts thereof, with other chemical components, such as physiologically acceptable carriers and excipients. The purpose of a pharmaceutical composition is to facilitate administration of a compound to an organism.

An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

The term "small molecule", as used herein, generally refers to an organic molecule that is less than about 2000 g/mol in molecular weight, less than about 1500 g/mol, less than about 1000 g/mol, less than about 800 g/mol, or less than about 500 g/mol. Small molecules are non-polymeric and/or non-oligomeric.

The term "prodrug" refers to an agent, including nucleic acids and proteins, which is converted into a biologically active form in vitro and/or in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N. J. (1962). Drug Latentiation in Jucker, ed. *Progress in Drug Research,* 4:221-294; Morozowich et al. (1977). Application of Physical Organic Principles to Prodrug Design in E. B. Roche ed. *Design of Biopharmaceutical Properties through Prodrugs and Analogs*, APhA; Acad. Pharm. Sci.; E. B. Roche, ed. (1977). *Bioreversible Carriers in Drug in Drug Design, Theory and Application*, APhA; H. Bundgaard, ed. (1985) *Design of Prodrugs*, Elsevier; Wang et al. (1999) Prodrug approaches to the improved delivery of peptide drug, *Curr. Pharm. Design.* 5(4):265-287; Pauletti et al. (1997). Improvement in peptide bioavailability: Peptidomimetics and Prodrug Strategies, *Adv. Drug. Delivery Rev.* 27:235-256; Mizen et al. (1998). The Use of Esters as Prodrugs for Oral Delivery of β-Lactam antibiotics, *Pharm. Biotech.* 11:345-365; Gaignault et al. (1996). Designing Prodrugs and Bioprecursors I. Carrier Prodrugs, *Pract. Med. Chem.* 671-696; M. Asgharnejad (2000). Improving Oral Drug Transport Via Prodrugs, in G. L. Amidon, P. I. Lee and E. M. Topp, Eds., *Transport Processes in Pharmaceutical Systems*, Marcell Dekker, p. 185-218; Balant et al. (1990) Prodrugs for the improvement of drug absorption via different routes of administration, *Eur. J. Drug Metab. Pharmacokinet.,* 15(2): 143-53; Balimane and Sinko (1999). Involvement of multiple transporters in the oral absorption of nucleoside analogues, *Adv. Drug Delivery Rev.,* 39(1-3):183-209; Browne (1997). Fosphenytoin (Cerebyx), *Clin. Neuropharmacol.* 20(1): 1-12; Bundgaard (1979). Bioreversible derivatization of drugs—principle and applicability to improve the therapeutic effects of drugs, *Arch. Pharm. Chemi.* 86(1): 1-39; H. Bundgaard, ed. (1985) *Design of Prodrugs*, New York: Elsevier; Fleisher et al. (1996). Improved oral drug delivery: solubility limitations overcome by the use of prodrugs, *Adv. Drug Delivery Rev.* 19(2): 115-130; Fleisher et al. (1985). Design of prodrugs for improved gastrointestinal absorption by intestinal enzyme targeting, *Methods Enzymol.* 112:

360-81; Farquhar D, et al. (1983). Biologically Reversible Phosphate-Protective Groups, *J. Pharm. Sci.,* 72(3): 324-325; Han, H. K. et al. (2000). Targeted prodrug design to optimize drug delivery, *AAPS PharmSci.,* 2(1): E6; Sadzuka Y. (2000). Effective prodrug liposome and conversion to active metabolite, *Curr. Drug Metab.,* 1(1):31-48; D. M. Lambert (2000) Rationale and applications of lipids as prodrug carriers, *Eur. J. Pharm. Sci.,* 11 Suppl. 2:S15-27; Wang, W. et al. (1999) Prodrug approaches to the improved delivery of peptide drugs. *Curr. Pharm. Des.,* 5(4):265-87.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

The term "copolymer" as used herein, generally refers to a single polymeric material that is comprised of two or more different monomers. The copolymer can be of any form, such as random, block, graft, etc. The copolymers can have any end-group, including capped or acid end groups.

The term "biodegradable" as used herein, generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

The term "hydrophilic", as used herein, refers to substances that have strongly polar groups that readily interact with water.

The term "hydrophobic", as used herein, refers to substances that lack an affinity for water; tending to repel and not absorb water as well as not dissolve in or mix with water.

The term "lipophilic", as used herein, refers to compounds having an affinity for lipids.

The term "mean particle size", as used herein, generally refers to the statistical mean particle size (diameter) of the particles in the composition. The diameter of an essentially spherical particle may be referred to as the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering. Two populations can be said to have a "substantially equivalent mean particle size" when the statistical mean particle size of the first population of nanoparticles is within 20% of the statistical mean particle size of the second population of nanoparticles; more preferably within 15%, most preferably within 10%.

The terms "monodisperse" and "homogeneous size distribution", as used interchangeably herein, describe a population of particles, microparticles, or nanoparticles all having the same or nearly the same size. As used herein, a monodisperse distribution refers to particle distributions in which 90% of the distribution lies within 5% of the mean particle size.

The term "nucleic acid" is a term of art that refers to a string of at least two base-sugar-phosphate combinations. For naked DNA delivery, a polynucleotide contains more than 120 monomeric units since it must be distinguished from an oligonucleotide. However, for purposes of delivering RNA, RNAi and siRNA, either single or double stranded, a polynucleotide contains 2 or more monomeric units. Nucleotides are the monomeric units of nucleic acid polymers. The term includes deoxyribonucleic acid (DNA) and ribonucleic acid (RNA) in the form of a messenger RNA, anti-sense, plasmid DNA, parts of a plasmid DNA or genetic material derived from a virus. Anti-sense is a polynucleotide that interferes with the function of DNA and/or RNA. The term nucleic acids—refers to a string of at least two base-sugar-phosphate combinations. Natural nucleic acids have a phosphate backbone, artificial nucleic acids may contain other types of backbones, but contain the same bases. Nucleotides are the monomeric units of nucleic acid polymers. The term includes deoxyribonucleic acid (DNA) and ribonucleic acid (RNA). RNA may be in the form of an tRNA (transfer RNA), snRNA (small nuclear RNA), rRNA (ribosomal RNA), mRNA (messenger RNA), anti-sense RNA, RNAi, siRNA, and ribozymes. The term also includes PNAs (peptide nucleic acids), phosphorothioates, and other variants of the phosphate backbone of native nucleic acids.

The term "siRNA" means a small inhibitory ribonucleic acid. The siRNA are typically less than 30 nucleotides in length and can be single or double stranded. The ribonucleotides can be natural or artificial and can be chemically modified. Longer siRNAs can comprise cleavage sites that can be enzymatically or chemically cleaved to produce siRNAs having lengths less than 30 nucleotides, typically 21 to 23 nucleotides. siRNAs share sequence homology with corresponding target mRNAs. The sequence homology can be 100 percent or less but sufficient to result is sequence specific association between the siRNA and the targeted mRNA. Exemplary siRNAs do not activate the interferon signal transduction pathway.

The term "inhibitory nucleic acid" means an RNA, DNA, or combination thereof that interferes or interrupts the translation of mRNA. Inhibitory nucleic acids can be single or double stranded. The nucleotides of the inhibitory nucleic acid can be chemically modified, natural or artificial.

II. Nanoparticles

Nanoparticles containing an aqueous core containing one or more nucleic acids, such as siRNA, and a shell containing one or more hydrophobic cationic materials, one or more amphiphilic materials, and one or more therapeutic, diagnostic, and/or prophylactic agents are. The hydrophobic cationic material and the hydrophobic portion of the amphiphilic material provide a non-polar polymer matrix for loading non-polar drugs, protect and promoting siRNA molecule retention inside the NP core, and control drug release. The hydrophilic portion of the amphiphilic material can form a corona around the particle which prolongs circulation of the particles in the blood stream and decreases uptake by the RES.

A. Shell

1. Amphiphilic Materials

The shell of the particles contains one or more amphiphilic materials. In some embodiments, the amphiphilic material contains one or more biodegradable oligomeric or polymeric segments or blocks and one or more hydrophilic oligomeric or polymeric segments or blocks. In particular embodiments, the biodegradable oligomeric or polymeric segment(s) or block(s) is hydrophobic. In some embodiments, the amphiphilic material is a hydrophobic, biodegradable polymer terminated with a hydrophilic block.

Biodegradable polymers can include polymers that are insoluble or sparingly soluble in water that are converted chemically or enzymatically in the body into water-soluble materials. Biodegradable polymers can include soluble polymers crosslinked by hydrolyzable cross-linking groups to render the crosslinked polymer insoluble or sparingly soluble in water.

Biodegradable polymers in the shell include, but are not limited to, polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polylactides, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene poly(ethylene glycol), poly (ethylene oxide), poly(ethylene terephthalate), poly(vinyl alcohols), poly(vinyl acetate, poly vinyl chloride polystyrene and polyvinylpryrrolidone, derivatives thereof, linear and branched copolymers and block copolymers thereof, and blends thereof.

Exemplary biodegradable polymers include, but are not limited to, polyesters, poly(ortho esters), poly(ethylene imines), poly(caprolactones), poly(hydroxybutyrates), poly(hydroxyvalerates), polyanhydrides, poly(acrylic acids), polyglycolides, poly(urethanes), polycarbonates, polyphosphate esters, polyphosphazenes, derivatives thereof, linear and branched copolymers and block copolymers thereof, and blends thereof. In particularly preferred embodiments the polymeric core contains biodegradable polyesters such as poly(lactic acid), poly(glycolic acid), and poly(lactic-co-glycolic acid).

In some embodiments, the biodegradable polymer in the shell is a hydrophobic biodegradable polymer. Examples of suitable hydrophobic polymers include, but are not limited to, polyhydroxyacids such as poly(lactic acid), poly(glycolic acid), and poly(lactic acid-co-glycolic acids); polyhydroxyalkanoates such as poly3-hydroxybutyrate or poly4-hydroxybutyrate; polycaprolactones; poly(orthoesters); polyanhydrides; poly(phosphazenes); poly(lactide-co-caprolactones); polycarbonates such as tyrosine polycarbonates; polyamides (including synthetic and natural polyamides), polypeptides, and poly(amino acids); polyesteramides; polyesters; poly(dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), as well as copolymers thereof.

In particularly preferred embodiments the polymeric core contains biodegradable polyesters or polyanhydrides such as poly(lactic acid), poly(glycolic acid), and poly(lactic-co-glycolic acid).

The molecular weight of the biodegradable oligomeric or polymeric segment can be varied to tailor the properties of polymeric particle shell. For example, the molecular weight of the biodegradable polymer can be varied to engineer nanoparticles possessing the required average particle size and degradation profile. The hydrophobic polymer segment has a molecular weight of between about 150 Da and about 100 kDa, more preferably between about 1 kDa and about 75 kDa, most preferably between about 5 kDa and about 50 kDa.

The amphiphilic material also contains one or more hydrophilic segments or blocks. In some embodiments, the hydrophilic segment(s) or block(s) function as stealth polymers in order to prolong circulation of the particles and avoid uptakes by the RES. Suitable stealth polymers include, but are not limited to, homo polymers or copolymers of polyalkene glycols, such as poly(ethylene glycol), polypropylene glycol), poly(butylene glycol), and acrylates and acrylamides, such as hydroxyethyl methacrylate and hydroxypropyl-methacrylamide.

The hydrophilic polymer segment typically has a molecular weight of between about 150 Da and about 20 kDa, more preferably between about 500 Da and about 10 kDa, most preferably between about 1 kDa and about 5 kDa.

In some embodiments, the amphiphilic material contains one or more blocks of a hydrophobic or more hydrophobic oligomer or polymer, such as PLA or PLGA, covalently bound to one or more blocks of PEG.

2. Hydrophobic Cationic Materials

The shell of the particles also contains a hydrophobic cationic material. In some embodiments, the cationic material is a material that is cationic at the time the hydrophobic cationic material is prepared or becomes cationic under physiological conditions. In some embodiments, the cationic material contains one or more amine containing moieties, such as amine containing small molecules, amine-containing polymers, such as PEI, and amine-containing macromolecules, such as dendrimers (see the structures below). The cationic moieties are functionalized with one or more hydrophobic/lipid moieties, such as lipophilic alkyl chains (e.g., $C_6$-$C_{30}$, preferably $C_6$-$C_{24}$, more preferably $C_6$-$C_{18}$), cholesterol, saturated or unsaturated fatty acids, etc. Exemplary amine-containing groups and hydrophobic groups which can be coupled to obtain hydrophobic cationic materials are shown below:

Amine-Containing Moiety:

Hydrophobic R' Containing Moieties:

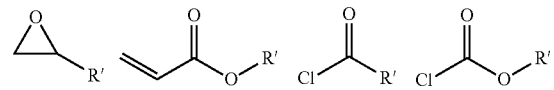

Coupled Amine-Containing Hydrophobic Materials:

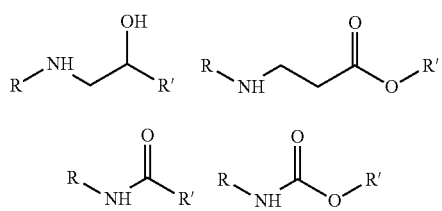

Example Amine-Containing Molecules, Polymer, and Dendrimer:

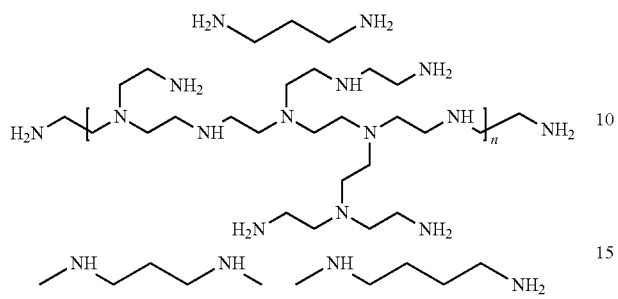

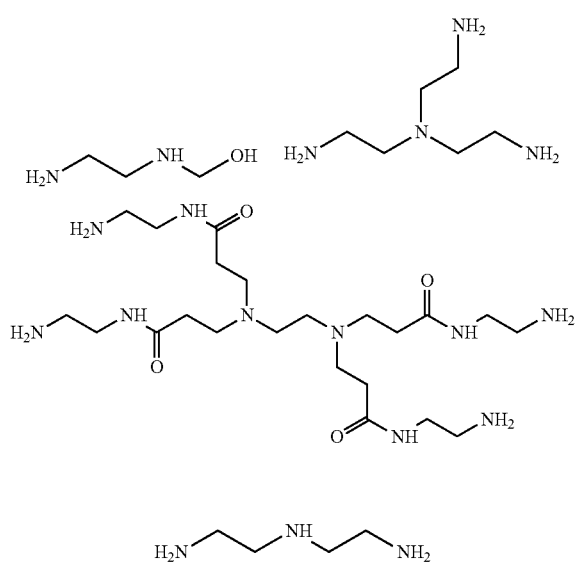

Example Hydrophobic R' Groups:

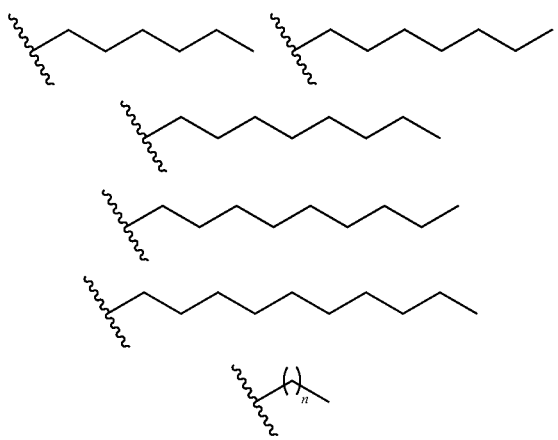

where n = 10-29

Lipid Tail C$_6$—C$_{30}$

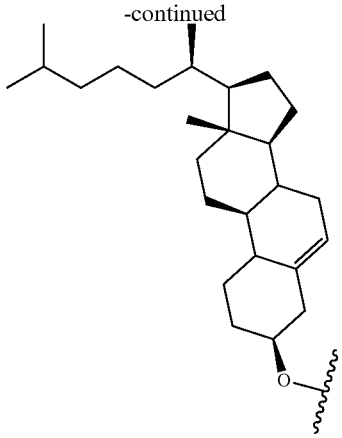

Cholesterol

The cationic moiety promotes retention of the siRNA in the core through electrostatic interaction while the hydrophobic moiety provides controlled release of the siRNA as well as any active agents in the shell.

3. Therapeutic, Prophylactic, and Diagnostic Agents

Any therapeutic, prophylactic, or diagnostic agent can be encapsulated in the particle core. In some embodiments the shell contains a therapeutic, prophylactic, or diagnostic agent. In other embodiments, the core contains a therapeutic, prophylactic, or diagnostic agent in addition to the siRNA. In still other embodiments, the shell and core contain a therapeutic, prophylactic, or diagnostic agent. In particular embodiments, the shell contains one or more non-polar therapeutic, prophylactic, and/or diagnostic agent The loading range for the agent within the particles is from about 0.01 to about 80% (agent weight/particle weight), preferably from 0.01% to about 50% (wt/wt), more preferably from about 0.01% to about 25% (wt/wt), even more preferably from about 0.01% to about 10% (wt/wt), most preferably from about 0.1% to about 5% (wt/wt).

For small molecules, the percent loading is typically from about 0.01% to about 20% (wt/wt), although higher loadings may be achieved for hydrophobic drugs and/or insoluble metals.

For large biomolecules, such as proteins and nucleic acids, typical loadings are from about 0.01% to about 10% (wt/wt), preferably from about 0.01% to about 5.0% (wt/wt), more preferably from about 0.01% to about 2.5% (wt/wt), most preferably from about 0.01% to about 1% (wt/wt). The loading can be calculated relative to the mass of the polymer, lipid, or inorganic particles.

The particles can include one or more chemotherapeutic agents for the treatment of cancer and other diseases. In some embodiment, the chemotherapeutic agent is hydrophobic and therefore is dispersed within the more hydrophobic shell of the particles. The biodegradable polymer and/or hydrophobic cationic material in the shell provide controlled release of the chemotherapeutic agent.

Chemotherapeutics includes, but not limited to, the following classes: alkylating agents, antimetabolites, anthracyclines, plant alkaloids, topoisomerase inhibitors, monoclonal antibodies, and other anti-tumor agents. In addition to the chemotherapeutic drugs described above, namely doxorubicin, paclitaxel, other suitable chemotherapy drugs include tyrosine kinase inhibitor imatinib mesylate (Gleevec® or Glivec®), cisplatin, carboplatin, oxaliplatin, mechloethamine, cyclophosphamide, chlorambucil, azathioprine, mercaptopurine, pyrimidine, vincristine, vinblastine, vinorelbine, vindesine, podophyllotoxin (L01CB), etoposide, docetaxel, topoisomerase inhibitors (L01CB and L01XX) irinotecan, topotecan, amsacrine, etoposide, etoposide phosphate, teniposide, dactinomycin, lonidamine, and monoclonal antibodies, such as trastuzumab (Herceptin®), cetuximab, bevacizumab and rituximab (Rituxan®), among others.

Additional exemplary active agents include PARP inhibitors, survivin inhibitors, estradiol, and dichloroacetate.

Other examples of active agents include, but are not limited to, antimicrobial agents, analgesics, anti-inflammatory agents, and other chemotherapeutic or anti-cancer agents. Antibiotics can be incorporated into the particle, such as vancomycin, which is frequently used to treat infections, including those due to methicillin resistant staph aureus (MRSA). The particle optionally includes cyclosporin, a lipophilic drug that is an immunosuppressant agent, widely used post-allogeneic organ transplant to reduce the activity of the patient's immune system and the risk of organ rejection (marketed by Novartis under the brand names Sandimmune®, the original formulation, and Neoral® for the newer microemulsion formulation). Particles comprising cyclosporine can be used in topical emulsions for treating keratoconjunctivitis sicca, as well. In this regard, particles with multifunctional surface domains incorporating such drugs can be designed to deliver equivalent dosages of the various drugs directly to the cancer cells, thus potentially minimizing the amount delivered generally to the patient and minimizing collateral damage to other tissues.

In some embodiments, the chemotherapeutic is a platinum-based chemotherapeutic or prodrug thereof. In particular embodiments, the chemotherapeutic is cisplatin or a prodrug thereof. The drug can be dispersed (e.g., non-covalently associated) in the polymeric shell or can be covalently bound to the polymeric shell.

In some embodiments, chemotherapeutic agent can be conjugated to a biodegradable polymer. For example, a cisplatin prodrug (platinum monosuccinate) was functionalized to a PLA having pendant hydroxyl groups. Similar approaches can be used for conjugation of other active agents. For example, for the development of polylactide with pendant oxaliplatin, the oxaliplatin prodrug can be synthesized with carboxyl groups at the axial position, which will be coupled to the PLA-OH. Polylactide with paclitaxel pendant groups was prepared by generating carboxyl group containing polylactide by treating PLA-OH with succinic anhydride, and this compound was coupled directly with hydroxyl groups of paclitaxel. In the case of tubacin-functionalized polymers, the same carboxyl group containing polylactides can be conjugated to the hydroxyl groups of tubacin.

B. Core

The particles contain an aqueous core surrounded by the more hydrophobic shell. The aqueous core contains one or more nucleic acids, such as siRNAs, shRNA, DNA antisense, DNA plasmid, peptides, therapeutic proteins, water soluble small drugs, or the mixture of those agents.

The inhibitory nucleic acids of certain embodiments are directed to target genes encoding proteins involved in DNA repair and the acquisition of multidrug resistance (MDR), for example in the treatment of cancer. The inhibitory nucleic acids disclosed herein include small inhibitory ribonucleic acids (siRNAs) that are typically less than 30 nucleotides in length, more typically 21 to 23 nucleotides in length, and can be single or double stranded. One strand of a double-stranded siRNA comprises at least a partial sequence complementary to a target mRNA. The ribonucleotides of the siRNA can be natural or artificial and can be chemically modified. Longer siRNAs can comprise cleavage sites that can be enzymatically or chemically cleaved to produce siRNAs having lengths less than 30 nucleotides. siRNAs share sequence homology with corresponding target mRNAs. The phosphate backbones of the siRNAs can be chemically modified to resist enzymatic degradation. The sequence homology can be about 100 percent or less, but sufficient to result is sequence specific association between the siRNA and the targeted mRNA.

Nucleic acids, in particular RNA, are known to participate in a form of post-transcriptional gene silencing termed "RNA interference" or RNAi. First observed in plants, reduction of expression of specific mRNA sequences was found to be inducible in *Drosophila melanogaster* and *Caenorhabditis elegans* by introduction of double-stranded RNA (dsRNA) molecules mimicking the sequence of the mRNA. The effect was found to be potent and extremely long-lived in these experimental model organisms, generally extending to the F1 progeny of a treated adult specimen. Additionally, the effect was found to be exquisitely sequence-specific; discrepancy of even a few base pairs between the dsRNA and the target mRNA virtually abolished the silencing.

Current models of RNAi divide the process of inhibition into broad "initiation" and "effector" stages. In the initiation step, input dsRNA is digested into 21-23 nucleotide small interfering RNAs (siRNAs), which have also been called "guide RNAs." Inhibitory nucleic acids can be enzymatically cleaved, for example, in vivo, to produce siRNAs from 10 to about 30 nucleotides, typically about 19 to about 23 nucleotides. In the effector step, the siRNA duplexes bind to a nuclease complex to form what is known as the RNA-induced silencing complex, or RISC. An ATP-depending unwinding of the siRNA duplex is required for activation of the RISC. The active RISC then targets the homologous transcript by base pairing interactions and cleaves the mRNA ~12 nucleotides from the 3' terminus of the siRNA. Additionally, the siRNAs can form a complex with additional proteins and/or cofactors to enzymatically cleave a target mRNA.

C. Targeting Moieties

The particles, such as the surface of the particles, can be modified to facilitate targeting through the attachment of targeting molecules. Exemplary target molecules include proteins, peptides, nucleic acids, lipids, saccharides, or polysaccharides that bind to one or more targets associated with an organ, tissue, cell, or extracellular matrix, or specific type of tumor or infected cell. The degree of specificity with which the particles are targeted can be modulated through the selection of a targeting molecule with the appropriate affinity and specificity. For example, a targeting moiety can be a polypeptide, such as an antibody that specifically recognizes a tumor marker that is present exclusively or in higher amounts on a malignant cell (e.g., a tumor antigen). Suitable targeting molecules that can be used to direct nanoparticles to cells and tissues of interest, as well as methods of conjugating target molecules to nanoparticles, are known in the art. See, for example, Ruoslahti, et al. *Nat. Rev. Cancer,* 2:83-90 (2002). Targeting molecules can also include neuropilins and endothelial targeting molecules, integrins, selectins, and adhesion molecules. Targeting molecules can be covalently bound to particles using a variety of methods known in the art. In some embodiments, the targeting moieties are covalently associated with the polymer, preferably via a linker cleaved at the site of delivery.

The nanoparticles can contain one or more polymer conjugates containing end-to-end linkages between the polymer and a targeting element or a detectable label. For example, a modified polymer can be a PLGA-PEG-peptide block polymer.

Examples of targeting moieties include peptides such as iRGD, LyP1; small molecule such as folate, aptamers and antibodies or their combinations at various molar ratios.

The targeting element of the nanoparticle can be an antibody or antigen binding fragment thereof. The targeting elements should have an affinity for a cell-surface receptor or cell-surface antigen on the target cells and result in internalization of the particle within the target cell.

The targeting element can specifically recognize and bind to a target molecule specific for a cell type, a tissue type, or an organ. The target molecule can be a cell surface polypeptide, lipid, or glycolipid. The target molecule can be a receptor that is selectively expressed on a specific cell surface, a tissue or an organ. Cell specific markers can be for specific types of cells including, but not limited to stem cells, skin cells, blood cells, immune cells, muscle cells, nerve cells, cancer cells, virally infected cells, and organ specific cells. The cell markers can be specific for endothelial, ectodermal, or mesenchymal cells. Representative cell specific markers include, but are not limited to cancer specific markers.

Additional targets that can be recognized by the targeting element include VEGF/KDR, Tie2, vascular cell adhesion molecule (VCAM), endoglin and $\alpha_5\beta_3$ integrin/vitronectin. The targeting peptides can be covalently associated with the polymer of the outer shell and the covalent association can be mediated by a linker.

Tumor-Specific and Tumor-Associated Antigens

In one embodiment the targeting element specifically binds to an antigen that is expressed by tumor cells. The antigen expressed by the tumor may be specific to the tumor, or may be expressed at a higher level on the tumor cells as compared to non-tumor cells. Antigenic markers such as serologically defined markers known as tumor associated antigens, which are either uniquely expressed by cancer cells or are present at markedly higher levels (e.g., elevated in a statistically significant manner) in subjects having a malignant condition relative to appropriate controls, are contemplated for use in certain embodiments.

Tumor-associated antigens may include, for example, cellular oncogene-encoded products or aberrantly expressed proto-oncogene-encoded products (e.g., products encoded by the neu, ras, trk, and kit genes), or mutated forms of growth factor receptor or receptor-like cell surface molecules (e.g., surface receptor encoded by the c-erb B gene). Other tumor-associated antigens include molecules that may be directly involved in transformation events, or molecules that may not be directly involved in oncogenic transformation events but are expressed by tumor cells (e.g., carcinoembryonic antigen, CA-125, melonoma associated antigens, etc.) (see, e.g., U.S. Pat. No. 6,699,475; Jager, et al., *Int. J. Cancer,* 106:817-20 (2003); Kennedy, et al., *Int. Rev. Immunol.,* 22:141-72 (2003); Scanlan, et al. *Cancer Immun.,* 4:1 (2004)).

Genes that encode cellular tumor associated antigens include cellular oncogenes and proto-oncogenes that are aberrantly expressed. In general, cellular oncogenes encode products that are directly relevant to the transformation of the cell, and because of this, these antigens are particularly preferred targets for immunotherapy. An example is the tumorigenic neu gene that encodes a cell surface molecule involved in oncogenic transformation. Other examples include the ras, kit, and trk genes. The products of proto-oncogenes (the normal genes which are mutated to form oncogenes) may be aberrantly expressed (e.g., overexpressed), and this aberrant expression can be related to cellular transformation. Thus, the product encoded by proto-oncogenes can be targeted. Some oncogenes encode growth factor receptor molecules or growth factor receptor-like molecules that are expressed on the tumor cell surface. An example is the cell surface receptor encoded by the c-erbB gene. Other tumor-associated antigens may or may not be directly involved in malignant transformation. These antigens, however, are expressed by certain tumor cells and may therefore provide effective targets. Some examples are carcinoembryonic antigen (CEA), CA 125 (associated with ovarian carcinoma), and melanoma specific antigens.

In ovarian and other carcinomas, for example, tumor associated antigens are detectable in samples of readily obtained biological fluids such as serum or mucosal secretions. One such marker is CA125, a carcinoma associated antigen that is also shed into the bloodstream, where it is detectable in serum (e.g., Bast, et al., *N. Eng. J. Med.,* 309:883 (1983); Lloyd, et al., *Int. J. Canc.,* 71:842 (1997). CA125 levels in serum and other biological fluids have been measured along with levels of other markers, for example, carcinoembryonic antigen (CEA), squamous cell carcinoma antigen (SCC), tissue polypeptide specific antigen (TPS), sialyl TN mucin (STN), and placental alkaline phosphatase (PLAP), in efforts to provide diagnostic and/or prognostic profiles of ovarian and other carcinomas (e.g., Sarandakou, et al., *Acta Oncol.,* 36:755 (1997); Sarandakou, et al., *Eur. J. Gynaecol. Oncol.,* 19:73 (1998); Meier, et al., *Anticancer Res.,* 17(4B):2945 (1997); Kudoh, et al., *Gynecol. Obstet. Invest.,* 47:52 (1999)). Elevated serum CA125 may also accompany neuroblastoma (e.g., Hirokawa, et al., *Surg. Today,* 28:349 (1998), while elevated CEA and SCC, among others, may accompany colorectal cancer (Gebauer, et al., *Anticancer Res.,* 17(4B):2939 (1997)).

The tumor associated antigen, mesothelin, defined by reactivity with monoclonal antibody K-1, is present on a majority of squamous cell carcinomas including epithelial ovarian, cervical, and esophageal tumors, and on mesotheliomas (Chang, et al., *Cancer Res.,* 52:181 (1992); Chang, et al., *Int. J. Cancer,* 50:373 (1992); Chang, et al., *Int. J. Cancer,* 51:548 (1992); Chang, et al., *Proc. Natl. Acad. Sci. USA,* 93:136 (1996); Chowdhury, et al., *Proc. Natl. Acad. Sci. USA,* 95:669 (1998)). Using MAb K-1, mesothelin is detectable only as a cell-associated tumor marker and has not been found in soluble form in serum from ovarian cancer patients, or in medium conditioned by OVCAR-3 cells (Chang, et al., *Int. J. Cancer,* 50:373 (1992)). Structurally related human mesothelin polypeptides, however, also include tumor-associated antigen polypeptides such as the distinct mesothelin related antigen (MRA) polypeptide, which is detectable as a naturally occurring soluble antigen in biological fluids from patients having malignancies (see WO 00/50900).

A tumor antigen may include a cell surface molecule. Tumor antigens of known structure and having a known or described function, include the following cell surface receptors: HER1 (GenBank Accession No. U48722), HER2 (Yoshino, et al., *J. Immunol.,* 152:2393 (1994); Disis, et al., Canc. Res., 54:16 (1994); GenBank Acc. Nos. X03363 and M17730), HER3 (GenBank Acc. Nos. U29339 and M34309), HER4 (Plowman, et al., *Nature,* 366:473 (1993); GenBank Acc. Nos. L07868 and T64105), epidermal growth factor receptor (EGFR) (GenBank Acc. Nos. U48722, and KO3193), vascular endothelial cell growth factor (GenBank No. M32977), vascular endothelial cell growth factor receptor (GenBank Acc. Nos. AF022375, 1680143, U48801 and X62568), insulin-like growth factor-I (GenBank Acc. Nos. X00173, X56774, X56773, X06043, European Patent No. GB 2241703), insulin-like growth factor-II (GenBank Acc. Nos. X03562, X00910, M17863 and M17862), transferrin receptor (Trowbridge and Omary, Proc. Nat. Acad. USA, 78:3039 (1981); GenBank Acc. Nos. X01060 and M11507), estrogen receptor (GenBank Acc. Nos. M38651, X03635, X99101, U47678 and M12674), progesterone receptor (GenBank Acc. Nos.

X51730, X69068 and M15716), follicle stimulating hormone receptor (FSH-R) (GenBank Acc. Nos. Z34260 and M65085), retinoic acid receptor (GenBank Acc. Nos. L12060, M60909, X77664, X57280, X07282 and X06538), MUC-1 (Barnes, et al., Proc. Nat. Acad. Sci. USA, 86:7159 (1989); GenBank Acc. Nos. M65132 and M64928) NY-ESO-1 (GenBank Acc. Nos. AJ003149 and U87459), NA 17-A (PCT Publication No. WO 96/40039), Melan-A/MART-1 (Kawakami, et al., Proc. Nat. Acad. Sci. USA, 91:3515 (1994); GenBank Ace. Nos. U06654 and U06452), tyrosinase (Topalian, et al., Proc. Nat. Acad. Sci. USA, 91:9461 (1994); GenBank Acc. No. M26729; Weber, et al., J. Clin. Invest, 102:1258 (1998)), Gp-100 (Kawakami, et al., Proc. Nat. Acad. Sci. USA, 91:3515 (1994); GenBank Acc. No. S73003, Adema, et al., J. Biol. Chem., 269:20126 (1994)), MAGE (van den Bruggen, et al., Science, 254:1643 (1991)); GenBank Acc. Nos. U93163, AF064589, U66083, D32077, D32076, D32075, U10694, U10693, U10691, U10690, U10689, U10688, U10687, U10686, U10685, L18877, U10340, U10339, L18920, U03735 and M77481), BAGE (GenBank Acc. No. U19180; U.S. Pat. Nos. 5,683,886 and 5,571,711), GAGE (GenBank Acc. Nos. AF055475, AF055474, AF055473, U19147, U19146, U19145, U19144, U19143 and U19142), any of the CTA class of receptors including in particular HOM-MEL-40 antigen encoded by the SSX2 gene (GenBank Acc. Nos. X86175, U90842, U90841 and X86174), carcinoembryonic antigen (CEA, Gold and Freedman, J. Exp. Med., 121:439 (1985); GenBank Acc. Nos. M59710, M59255 and M29540), and PyLT (GenBank Acc. Nos. J02289 and J02038); p97 (melanotransferrin) (Brown, et al., J. Immunol., 127:539-46 (1981); Rose, et al., Proc. Natl. Acad. Sci. USA, 83:1261-61 (1986)).

Additional tumor associated antigens include prostate surface antigen (PSA) (U.S. Pat. Nos. 6,677,157; 6,673,545); β-human chorionic gonadotropin β-HCG) (McManus, et al., Cancer Res., 36:3476-81 (1976); Yoshimura, et al., Cancer, 73:2745-52 (1994); Yamaguchi, et al., Br. J. Cancer, 60:382-84 (1989): Alfthan, et al., Cancer Res., 52:4628-33 (1992)); glycosyltransferase β-1,4-N-acetylgalactosaminyl-transferases (GalNAc) (Hoon, et al., Int. J. Cancer, 43:857-62 (1989); Ando, et al., Int. J. Cancer, 40:12-17 (1987); Tsuchida, et al., J. Natl. Cancer, 78:45-54 (1987); Tsuchida, et al., J. Natl. Cancer, 78:55-60 (1987)); NUC18 (Lehmann, et al., Proc. Natl. Acad. Sci. USA, 86:9891-95 (1989); Lehmann, et al., Cancer Res., 47:841-45 (1987)); melanoma antigen gp75 (Vijayasardahi, et al., J. Exp. Med., 171:1375-80 (1990); GenBank Accession No. X51455); human cytokeratin 8; high molecular weight melanoma antigen (Natali, et al., Cancer, 59:55-63 (1987); keratin 19 (Datta, et al., J. Clin. Oncol., 12:475-82 (1994)).

Tumor antigens of interest include antigens regarded in the art as "cancer/testis" (CT) antigens that are immunogenic in subjects having a malignant condition (Scanlan, et al., Cancer Immun., 4:1 (2004)). CT antigens include at least 19 different families of antigens that contain one or more members and that are capable of inducing an immune response, including but not limited to MAGEA (CT1); BAGE (CT2); MAGEB (CT3); GAGE (CT4); SSX (CT5); NY-ESO-1 (CT6); MAGEC (CT7); SYCP1 (C8); SPANXB1 (CT11.2); NA88 (CT18); CTAGE (CT21); SPA17 (CT22); OY-TES-1 (CT23); CAGE (CT26); HOM-TES-85 (CT28); HCA661 (CT30); NY-SAR-35 (CT38); FATE (CT43); and TPTE (CT44).

Additional tumor antigens that can be targeted, including a tumor-associated or tumor-specific antigen, include, but not limited to, alpha-actinin-4, Bcr-Ab1 fusion protein, Casp-8, beta-catenin, cdc27, cdk4, cdkn2a, coa-1, dck-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pm1-RARα fusion protein, PTPRK, K-ras, N-ras, Triosephosphate isomeras, Bage-1, Gage 3,4,5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel -40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, and TPS. Other tumor-associated and tumor-specific antigens are known to those of skill in the art and are suitable for targeting by the fusion proteins.

1. Peptide Targeting Elements

In a preferred embodiment, the targeting element is a peptide. Specifically, the plaque targeted peptide can be, but is not limited to, one or more of the following: RGD, iRGD(CRGDK/RGPD/EC) (SEQ ID NO:1), LyP-1, P3(CKGGRAKDC) (SEQ ID NO:2), or their combinations at various molar ratios. The targeting peptides can be covalently associated with the polymer and the covalent association can be mediated by a linker.

2. Antibody Targeting Elements

The targeting element can be an antibody or an antigen-binding fragment thereof. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. The antigen binding portion of the antibody can be any portion that has at least one antigen binding site, such as Fab, F(ab')$_2$, dsFv, sFv, diabodies, and triabodies. In certain embodiments, the antibody is a single chain antibody.

3. Aptamer Targeting Elements

Aptamers are oligonucleotide or peptide sequences with the capacity to recognize virtually any class of target molecules with high affinity and specificity. Aptamers bind to targets such as small organics, peptides, proteins, cells, and tissues. Unlike antibodies, some aptamers exhibit stereoselectivity. The aptamers can be designed to bind to specific targets expressed on cells, tissues or organs.

D. Particle Properties

The particles may have any diameter. The particles can have a diameter of about 10 nm to about 10 microns, about 10 nm to about 1 micron, about 10 nm to about 500 nm, about 20 nm to about 500 nm, or about 25 nm to about 250 nm. In preferred embodiments, the particle is a nanoparticle having a diameter from about 25 nm to about 250 nm. In more preferred embodiments, the particles are nanoparticles having a diameter from about 180 nm to about 250 nm, preferably from about 180 nm to about 230 nm. The polydispersity is from about 0.05 to 0.30, preferably from about 0.05 to about 0.25, more preferably from about 0.05 to about 0.20, more preferably from about 0.05 to about 0.15, most preferably from about 0.05 to about 0.10.

The particles may have any zeta potential. The particles can have a zeta potential from −300 mV to +300 mV, −100 mV to +100 mV, from −50 mV to +50 mV, from −40 mV to +40 mV, from −30 mV to +30 mV, from −20 mV to +20 mV, from −10 mV to +10 mV, or from −5 mV to +5 mV. The particles can have a negative or positive zeta potential. In some embodiments the particles have a substantially neutral zeta potential, i.e. the zeta potential is approximately 0 mV. In preferred embodiments the particles have a zeta potential of approximately −30 to about 30 mV, preferably from about −20 to about 20 mV, more preferably from about −10 to about 10 mV.

III. Pharmaceutical Compositions

The particles can be formulated with appropriate pharmaceutically acceptable carries to into pharmaceutical compositions for administration to an individual in need thereof. The formulations can be administered enterally (e.g., oral) or parenterally (e.g., by injection or infusion). Other routes of administration include, but are not limited to, transdermal.

The compounds can be formulated for parenteral administration. "Parenteral administration", as used herein, means administration by any method other than through the digestive tract or non-invasive topical or regional routes. For example, parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

Enteral formulations are prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include hydrophobic or hydrophilic polymers and pH dependent or independent polymers. Preferred hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins.

Carrier also includes all components of the coating composition which may include plasticizers, pigments, colorants, stabilizing agents, and glidants. Formulations can be prepared using one or more pharmaceutically acceptable excipients, including diluents, preservatives, binders, lubricants, disintegrators, swelling agents, fillers, stabilizers, and combinations thereof.

Delayed release dosage formulations can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

Stabilizers are used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

IV. Methods of Making

A. Hydrophobic Cationic Moieties

The hydrophobic cationic moieties can be prepared using techniques known in the art. For example, amine containing small molecules, polymers, (e.g., PEI), and/or dendrimers can be functionalized with one or more hydrophobic groups, such as lipophilic alkyl groups, cholesterol, or combinations thereof. These groups can be introduced by reaction the amine with the reactive derivative of the hydrophobic moiety, such as chloroformate, acid chloride, acrylates, acrylamides, and epoxide-terminated compounds.

B. Particles

In some embodiments, the chemotherapeutic agent is covalently bound to the amphiphilic material used to form the particle shell. Polymer-drug conjugates can be prepared using synthetic methods known in the art. The appropriate route for synthesis of a given polymer-drug conjugate can be determined in view of a number of factors, such as the structure of the polymer-drug conjugate, the composition of the polymer segments which make up the polymer-drug conjugate, the identity of the one or more drugs attached to the polymer-drug conjugate, as well as the structure of the conjugate and its components as it relates to compatibility of functional groups, protecting group strategies, and the presence of labile bonds. In addition to the synthetic methodologies discussed below, alternative reactions and strategies useful for the preparation of the polymer-drug conjugates disclosed herein are known in the art. See, for example, March, "Advanced Organic Chemistry," 5th Edition, 2001, Wiley-Interscience Publication, New York).

Methods of making polymeric particles are known in the art. Common microencapsulation techniques include, but are not limited to, spray drying, interfacial polymerization, hot melt encapsulation, phase separation encapsulation (spontaneous emulsion microencapsulation, solvent evaporation microencapsulation, and solvent removal microencapsulation), coacervation, low temperature microsphere formation, and phase inversion nanoencapsulation (PIN). A brief summary of these methods is presented below.

In some embodiments, the particles are prepared using an emulsion-based technique. In particular embodiments, the particles are prepared using a double emulsion solvent evaporation technique. For example, the amphiphilic material and the hydrophobic cationic material are dissolved in a suitable organic solvent, such as methylene chloride or dichloromethane (DCM), with or without a therapeutic agent. The siRNA is reconstituted in purified water, such as HyPure™ molecular biology grade water (Hyclone Laboratories, Inc., Logan, Utah). The siRNA solution is added dropwise to the solution of the amphiphilic material and the hydrophobic cationic material and emulsified to form a first emulsion. The emulsion is added to an aqueous solution of surfactant, such as PVA, to form a double emulsion. The final emulsion is added to water and stirred for an extended period of time (e.g., 3 hours) to allow the organic solvent to evaporate and the particles to harden. Residual organic solvent and/or unencapsulated molecules are removed by washing. Other emulsion emulsion-based procedures are described below.

1. Phase Separation Microencapsulation

In phase separation microencapsulation techniques, a polymer solution is stirred, optionally in the presence of one or more active agents to be encapsulated. While continuing to uniformly suspend the material through stirring, a non-solvent for the polymer is slowly added to the solution to decrease the polymer's solubility. Depending on the solubility of the polymer in the solvent and nonsolvent, the polymer either precipitates or phase separates into a polymer rich and a polymer poor phase. Under proper conditions, the polymer in the polymer rich phase will migrate to the interface with the continuous phase, encapsulating the active agent(s) in a droplet with an outer polymer shell.

2. Spontaneous Emulsion Microencapsulation

Spontaneous emulsification involves solidifying emulsified liquid polymer droplets formed above by changing temperature, evaporating solvent, or adding chemical cross-linking agents. The physical and chemical properties of the encapsulant, as well as the properties of the one or more active agents optionally incorporated into the nascent particles, dictates suitable methods of encapsulation. Factors such as hydrophobicity, molecular weight, chemical stability, and thermal stability affect encapsulation.

3. Solvent Evaporation Microencapsulation

Methods for forming microspheres using solvent evaporation techniques are described in E. Mathiowitz et al., *J. Scanning Microscopy*, 4:329 (1990); L. R. Beck et al., *Fertil. Steril.*, 31:545 (1979); L. R. Beck et al, *Am. J. Obstet. Gynecol.*, 135(3) (1979); S. Benita et al., *J. Pharm. Sci.*, 73:1721 (1984); and U.S. Pat. No. 3,960,757 to Morishita et al. The polymer is dissolved in a volatile organic solvent, such as methylene chloride. One or more active agents to be incorporated are optionally added to the solution, and the mixture is suspended in an aqueous solution that contains a surface active agent such as poly(vinyl alcohol). The resulting emulsion is stirred until most of the organic solvent evaporated, leaving solid microparticles/nanoparticles. This method is useful for relatively stable polymers like polyesters and polystyrene.

4. Phase Inversion Nanoencapsulation (PIN)

Nanoparticles can also be formed using the phase inversion nanoencapsulation (PIN) method, wherein a polymer is dissolved in a "good" solvent, fine particles of a substance to be incorporated, such as a drug, are mixed or dissolved in the polymer solution, and the mixture is poured into a strong non solvent for the polymer, to spontaneously produce, under favorable conditions, polymeric microspheres, wherein the polymer is either coated with the particles or the particles are dispersed in the polymer. See, e.g., U.S. Pat. No. 6,143,211 to Mathiowitz, et al. The method can be used to produce monodisperse populations of nanoparticles and microparticles in a wide range of sizes, including, for example, about 100 nanometers to about 10 microns.

5. Microfluidics

Nanoparticles can be prepared using microfluidic devices. A polymeric material is mixed with a drug or drug combinations in a water miscible organic solvent. The water miscible organic solvent can be one or more of the following: acetone, ethanol, methanol, isopropyl alcohol, acetonitrile and Dimethyl sulfoxide (DMSO). The resulting mixture solution is then added to an aqueous solution to yield nanoparticle solution. The targeted peptides or fluorophores or drugs may be associated with the surface of, encapsulated within, surrounded by, and/or distributed throughout the polymeric matrix of the particles.

V. Methods of Use

The particles can be used for the co-delivery of an effective amount of a nucleic acid, such as siRNA, and a therapeutic, diagnostic, and/or prophylactic agent. The therapeutic, diagnostic, and/or prophylactic agent can be a small molecule, a biomolecule or macromolecules, or combinations thereof. In one embodiment, the particles contain one or more siRNA that target genes encoding proteins involved in DNA repair and/or the acquisition of multidrug resistance (MDR).

The particles described here exhibit excellent encapsulation efficiency (EE %) of siRNA compared to the same nanoparticles without the hydrophobic cationic material. In some embodiments, the EE is at least about 20, 25, 30, 35, 40, 45, 50, 55, 60, 65, 70, 75, 80, 85, 90, 95, 96, 96, 98, or 99%. In contrast, particles lacking the hydrophobic cationic moiety had EE of about 6-10%.

The particles are able to release siRNA and a small molecule therapeutic in a controlled manner. In some embodiments, the particles release about 5, 8, 10, 12, 15, or 20% of the small molecule therapeutic over about 2, 3, 4, 5, or 6 hours, followed by sustained release over about 6, 7, 8, 9, 10, 11, or 12 hours. In some embodiments, the particles release about 75, 80, 85, 90, or 95% of the encapsulated small molecule therapeutic over about one week. The particles can release about 20, 25, 30, 35, 40, 45, 50, 55, or 60% of the encapsulated siRNA over about 20, 22, 24, 26, 28, 30, 32, 34, or 36 hours and about 75, 80, 85, 90, or 95% of the encapsulated siRNA over about 5, 6, 7, 8, 9, or 10 days.

Particles containing the siRNA siLuc showed increased silencing of luciferase expression as a function of concentration. When a dose of siRNA at or above 25 nanograms (ng) was used, NP(siLuc) achieved greater than 95% luciferase knockdown, a more efficient silencing efficacy than the commercially available liposome-based lipoplex (Lipo2000-siRNA complex). It should also be noted that no evidence of cellular toxicity was observed by the XTT (2,3-Bis-(2-Methoxy-4-Nitro-5-Sulfophenyl)-2H-Tetrazolium-5-Carboxanilide) assay under all the conditions used for in vitro transfection experiments.

The particles exhibited significant activity in inhibiting tumor growth. For example, the bioluminescence intensity from the control group mice increased rapidly from day 0 to day 3 with day 3 being a near 64% increase in intensity compared to day 0. In contrast, the tumors treated with NP(siLuc) showed a drastic decrease in bioluminescence intensity one-day post injection and increased in the following days. An 80% decrease in luciferase expression in the treated group one day post injection. Furthermore, the bioluminescence intensity of days 2 and 3 relative to day 0 remains a fractional part (71.4% and 85.7%, respectively), indicating a sustained gene silencing effect. These results suggest that the NPs are capable of delivering siRNA to inhibit luciferase expression in vivo.

The particles also exhibited sustained knockdown efficiency in a LNCaP tumor model. A qRT-PCR assay revealed a sustained knockdown efficiency of up to 87% for both genes REV1 and REV3L in LNCaP cells over the course of three days. A similar gene silencing efficacy was observed in MDA-MB-231 cells. Notably, these developed NPs are capable of simultaneously targeting multiple genes. An escalating-dose experiment in LNCaP cells to examine the effects of NP-mediated REV1/REV3L suppression on tumor cell chemosensitivity using four different formulations: (i) compound 1 in solution form, (ii) compound 1 encapsulated NP [NP(compound 1)], (iii) NP(siREV1, siREV3L) with compound 1 in solution, and (iv) NP(siREV1, siREV3L, compound 1). Prior to treatment with the two siRNA-containing NP formulations, the cells were transfected with NP(siREV1, siREV3L) for 24 hours in order to achieve substantial levels of Rev 1 and Rev3L suppression. The transfected cells were then treated with the two different siRNA-containing formulations with escalating-dose of compound 1. The first formulation consists of NP(siREV1, siREV3L) with compound 1 in solution form, whereas the second contains compound 1 within the NP [NP(siREV1, siREV3L, compound 1)].

A comparison of the dose-response curves revealed significantly lower EC50 values for all three NP formulations when compared to free drug in solution form. As expected, the cells treated with NP(siREV1, siREV3L) exhibited better dose-response to free drug than the untreated cells, thus providing evidence for the enhanced chemosensitization of prostate cancer cells through REV1 and REV3L suppression. Similarly, inclusion of the REV1/REV3L siRNAs in NPs resulted in improved tumor cell response to compound 1-loaded NPs compared to NP(scrambled siRNA, compound 1).

EXAMPLES

Materials and Methods

Materials

N-hydroxysuccinimide (NHS), 1-ethyl-3-[3-dimethylaminopropyl]carbodiimide hydrochloride (EDC), 1,2-epoxytetradecane, ethylenediamine core-PAMAM generation 0 dendrimer, decanoic anhydride and cis,cis,trans-[Pt(NH$_3$)$_2$Cl$_2$(OH)$_2$] were purchased from Aldrich.

PLGA with acid end groups was purchased from Adsorbable Polymers International.

A PEG polymer of molecular weight 3,400 with a terminal amine and carboxylic group (NH$_2$-PEG-COOH) was purchased from JenKem Technology USA.

siRNAs targeting luciferase (siLuc), Rev1 (siREV1) and Rev3L (siREV3L) were synthesized by and purchased from Dharmacon. Cy3-labeled siRNA was purchased from IDT. The siRNA sequences are as follows:

siLuc sense: 5'-CUUACGCUGAGUACUUCGA-3'; (SEQ ID NO:3);
antisense: 5'-UCGAAGUACUCAGCGUAAG-3'; (SEQ ID NO:4);
siREV1 sense: 5'-GCUGUAUAAUGCAUGUUGAUA-3'; (SEQ ID NO:5);
antisense: 5'-UAUCAACAUGCAUUAUACAGC-3'; (SEQ ID NO:6);
siREV3L sense: 5'-UCUUCUUGCUGGUUUGGAAAG-3'; (SEQ ID NO:7);
amtisense: 5'-CUUUCCAAACCAGCAAGAAGA-3'; (SEQ ID NO:8);

Instruments $^1$H, $^{13}$C, and $^{195}$Pt NMR spectra were recorded on a Bruker AVANCE-400 spectrometer with a Spectro Spin superconducting magnet in the MIT Department of Chemistry Instrumentation Facility.

ESI-MS analyses were performed on an Agilent 1100 series instrument. Atomic absorption spectroscopic measurements were taken on a Perkin-Elmer AAnalyst 300 spectrometer.

Lipofectamine™ 2000, and Quant-iT™ RiboGreen® RNA quantitation reagent were purchased from Invitrogen (Carlsbad, Calif.).

Dual-Glo™ Luciferase Assay System was purchased from Promega (Madison, Wis.).

Methods

General Cell Culture. A HeLa cell line stably expressing firefly and Renilla luciferase (Dual-Luc HeLa) was obtained from Alnylam Pharmaceuticals, Inc. The cells were maintained in Dulbecco's Modified Eagle's Medium (DMEM, Invitrogen) with high glucose, 10 v/v % FBS, 500 µg/mL zeocin, and 0.5 µg/mL puromycin. LNCaP and MDA-MB-231 cell lines (both bioluminescent and non-bioluminescent) were purchased from the American Type Culture Collection (ATCC, Manassas, Va.). Cells lines were cultured in RPMI-1640 media (Invitrogen, Carlsbad, Calif.) supplemented with 10% FBS and 1% penicillin/streptomycin. Cells and biological experiments were conducted at 37° C. in 5% CO2.

Animals. All animals were obtained from Charles River Laboratory. The animals were allowed free access to sterile food pellets and water. All in vivo studies were performed in accordance with National Institutes of Health Animal Care guidelines.

Example 1

Synthesis of Hydrophobic Cationic Component (G0-C14)

G0-C14 was synthesized by reacting 1,2-epoxytetradecane with generation 0 of ethylenediamine core-PAMAM dendrimer according to a known procedure. In order to increase the proportion of products with one less tail than the total possible for a given amine monomer, a substoichiometric amount of 1,2-epoxytetradecane was added to PAMAM dendrimer at a molar ratio of 7:1. The mixture was reacted under vigorous stirring at 90° C. for 2 days. The crude reaction mixture was separated by chromatography on silica with a gradient elution from CH$_2$Cl$_2$ to 75:22:3 CH$_2$Cl$_2$/MeOH/NH$_4$OH. The purified product was characterized by $^1$H NMR.

Figure 1B:
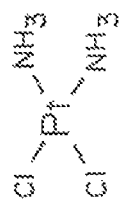
FIG. 1B is the chemical structure of the hydrophobic platinum (IV) compound 1 and the chemistry by which the active drug, cisplatin, is released, after reduction in the cell.
Figure 1B:
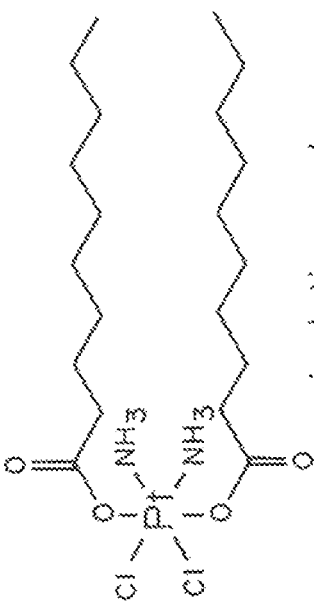
Figure 1C:
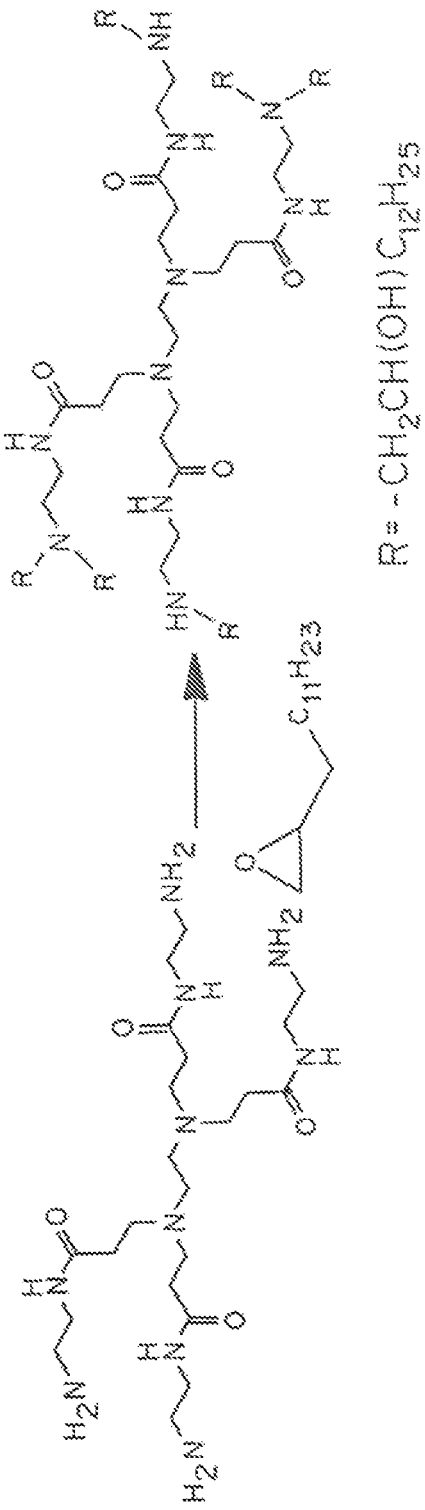
FIG. 1C is the scheme for the synthesis of G0-C14 through ring-opening of 1,2-epoxytetradecane by ethylenediamine core-PAMAM generation 0 dendrimer.
Figure 1D:
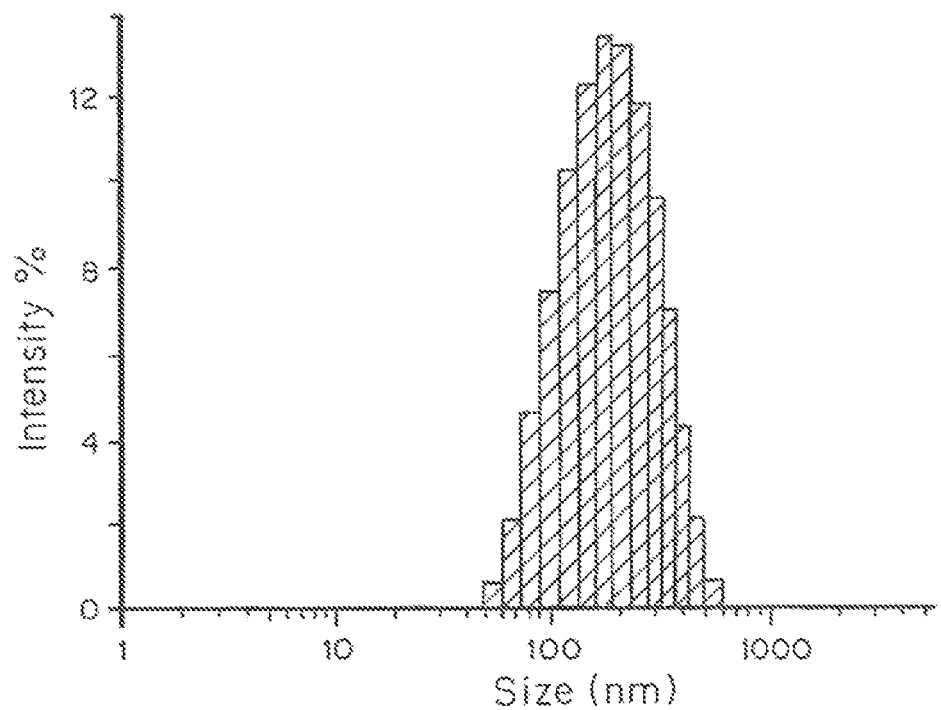
FIG. 1D is a graph showing the size distribution of the NPs containing both compound 1 and siRNA determined by dynamic light scattering (DLS).

The design and preparation of polymer/G0-C14 hybrid NPs are shown in FIGS. 1A-C. To facilitate siRNA encapsulation, cationic lipid-like molecules termed G0-C14 was synthesized through ring-opening of 1,2-epoxytetradecane by generation 0 of poly(amidoamine) (PAMAM) dendrimers (FIG. 1C). NPs were prepared through self-assembly of PLGA-b-PEG and the resulting G0-C14 using a double emulsion-solvent evaporation method. The generation 0 of PAMAM dendrimer was used for the cationic lipid preparation due to its minimal cytotoxicity compared to higher generations, while still providing sufficient positive charge to entrap the siRNA therapeutic agent. It has been shown that lipid-like materials, termed lipidoids, containing a 14 carbon tail are ideal for siRNA delivery; thus, 1,2-epoxytetradecane was selected for synthesis of G0-C14.

Example 2

Synthesis of cis,cis,trans-[Pt(NH$_3$)$_2$Cl$_2$(OOC(CH$_2$)$_8$CH$_3$)$_2$] (Compound 1)

Decanoic anhydride (0.41 g, 1.26 mmol, 3.8 equiv) was added to a solution of cis,cis,trans-[Pt(NH$_3$)$_2$Cl$_2$(OH)$_2$] (0.11 g, 0.33 mmol) in 10 mL DMF and the mixture was then stirred at 55° C. After 16 h, unreacted cis,cis,trans-[Pt(NH$_3$)$_2$Cl$_2$(OH)$_2$] was removed by the filtration, and the resulting yellow solution was then reduced to 3 mL under reduced pressure. This concentrated solution was then added dropwise to a rapidly stirring volume of diethyl ether (50 ml) forming a pale yellow precipitate. The buff-colored powder was filtered and washed twice with 30 mL of diethylether. The final product was dried in a desiccator. Pale yellow solid. Yield: 65% (0.138 g, 0.21 mmol). ESI-MS m/z calculated (M-H)$^-$: 641.2, found: 641.1. $^1$H NMR (DMSO-d$_6$): δ 0.85 (t, 6H, J=8.8 Hz), 1.22 (m 24H), 1.44 (q, 4H, J=8.2 Hz), 2.19 (t, 4H, J=8 Hz), 6.53 (s, 6H). $^{13}$C NMR (DMSO-d$_6$): δ 14.15, 22.11, 25.37, 28.66, 28.97, 31.47, 35.86, 180.02. $^{195}$Pt NMR (DMSO-d$_6$): δ 1217.76. Anal. Calcd. for C$_{20}$H$_{44}$Cl$_2$N$_2$O$_4$Pt: C, 37.38; H, 6.90; N, 4.36; Found: C, 37.38; H, 7.08; N, 4.71.

Compound 1 was designed and synthesized as a Pt(IV) prodrug because its hydrophobicity allowed for encapsulation within PLGA-b-PEG NPs while being sufficiently soluble in organic solvents like DMSO and dichloromethane (DCM), which is required for Pt(IV)-encapsulated NP preparation. Additionally, Pt(IV) complexes can be reduced in the intracellular milieu to yield the cytotoxic Pt(II) species through a reductive elimination of axial ligands. The redox potential for the reduction of a Pt(IV) prodrug, which is an analog of 1, has been previously investigated at various pH conditions. Electrochemical studies have demonstrated a positive shift of its reduction potential at pH 6, indicating that the acidic intracellular environment in cancer cells will facilitate reduction of the Pt(IV) compound and the release of cisplatin. Thus, Pt(IV) prodrugs provide an attractive alternative to the existing portfolio of Pt(II) drugs.

Example 3

Preparation and Characterization of NPs Containing siRNAs and Compound 1

Materials and Methods

Copolymer PLGA-b-PEG was synthesized by the amide coupling of HOOC-PEG-NH$_2$ to PLGA-COOH in methylene chloride as previously described. The NPs encapsulated with a combination payload of siRNAs and compound 1 was formulated via double emulsion solvent evaporation technique. In brief, copolymer PLGA-b-PEG and G0-C14 were co-dissolved in dichloromethane (DCM) with or without compound 1. siRNAs was reconstituted in HyPure™ molecular biology grade water (Hyclone Laboratories, Inc., Logan, Utah). The siRNA solution (0.4 mL) was added drop-wise into 1 mL PLGA-b-PEG and G0-C14 solution and emulsified by probe sonication to form the first emulsion. Next, the emulsified mixture was added into 3 mL aqueous solution containing 1% PVA, followed by probe sonication to form the double emulsion. The final emulsion solution was poured into 15 mL water and stirred for 3 hours to allow the DCM solvent to evaporate and the particles to harden. The remaining organic solvent and free molecules were removed by washing the particle solution three times using an Amicon Ultra-4 centrifugal filter (Millipore, Billerica, Ma.) with a molecular weight cutoff of 100 kDa. The NP size and zeta potential were determined by using a ZetaPALS dynamic light-scattering detector (15 mW laser, incident beam of 676 nm; Brookhaven Instruments Corporation, Holtsville, N.Y). Samples for TEM were stained with 1% uranyl acetate and observed using a JEOL 2011 at 200 kV. The Pt content in the NPs was measured by AAS. The siRNA in the NPs was analyzed by using Quant-iT™ RiboGreen assay according to the manufacturer's protocol. Drug loading is defined as the mass fraction of drug in the nanoparticles, whereas entrapment efficiency (EE) is the fraction of initial drug that is encapsulated by the nanoparticles.

Results

After the incorporation of G0-C14, the resultant hybrid NPs exhibited simultaneous entrapment of siRNA (up to 99%) and compound 1. In contrast, PLGA-b-PEG NPs were only able to encapsulate approximately 6-10% of the initial siRNA, suggesting G0-C14 drastically enhanced the entrapment of siRNA within NPs. The entrapment efficiencies of Cy3-labeled siRNA at various weight ratios of G0-C14 to siRNA are calculated based on fluorescence measurement and shown in Table 1.

TABLE 1

Entrapment efficiencies of Cy3-labeled siRNA at various weight ratios of G0-C14 to siRNA

| G0-C14/siRNA Weight Ratio* | Encapsulation Efficacy (EE %) | Size (nm) | Polydispersity (PDI) | Zeta Potential (mv) |
|---|---|---|---|---|
| 10:1 | 87.0 ± 5.0 | 210 ± 8.5 | 0.23 ± 0.07 | 15.7 ± 4.5 |
| 20:1 | 95.0 ± 4.0 | 220 ± 12.5 | 0.18 ± 0.04 | 17.6 ± 3.1 |
| 30:1 | 99.0 ± 3.0 | 185 ± 10 | 0.10 ± 0.06 | 25.0 ± 2.6 |

The size of the NPs range from 180 nm to 220 nm with polydispersity index (PDI) at or lower than 0.23. In addition, the zeta potential of the resultant NPs increased with the weight ratio of G0-C14 to siRNA. Within the range of the tested parameters, the weight ratio of G0-C14 to siRNA had little impact on the loading efficiency of compound 1, which remained around 10%. For the following studies, NPs with a fixed G0-C14/siRNA weight ratio of 20 were used. The NPs showed compact and spherical morphology with a mean diameter of around 200 nm.

Example 4

Release of Compound 1 and siRNA From the NPs

Materials and Methods

To determine release kinetics, Cy3-labeled siRNA was first encapsulated into the NPs. A suspension of NPs in phosphate buffered saline (PBS) was aliquotted (100 µL) into several semipermeable minidialysis tubes (molecular mass cutoff 100 kDa; Pierce) and dialyzed against frequently renewed PBS (pH 7.4) at 37° C. with gentle stirring. At a predetermined time, an aliquot of the NP suspension was removed, and the platinum content was analyzed by AAS. For siRNA quantification, a standard curve correlating fluorescence and Cy3-siRNA concentration was used to determine the amount of siRNA encapsulated within the NPs. The fluorescence intensity was measured by Synergy HT multi-mode microplate reader (ex/em 530/590 nm, BioTek Instruments Inc., Winooski, Vt.).

The release kinetics of the Pt(IV) prodrug 1 and siRNA from the NPs were measured. In this system, the Pt(IV) compound 1 is homogeneously dispersed by encapsulation throughout the hydrophobic PLGA layer and is released through a diffusion-controlled process and polymer degradation. Release studies were conducted by dialyzing NPs containing both compound 1 and siRNA against 2 L of frequently renewed PBS at pH 7.4 and 37° C. to mimic physiological conditions. The amount of platinum released from the NPs was measured by atomic absorption spectroscopy (AAS).

Results

Figure 2:
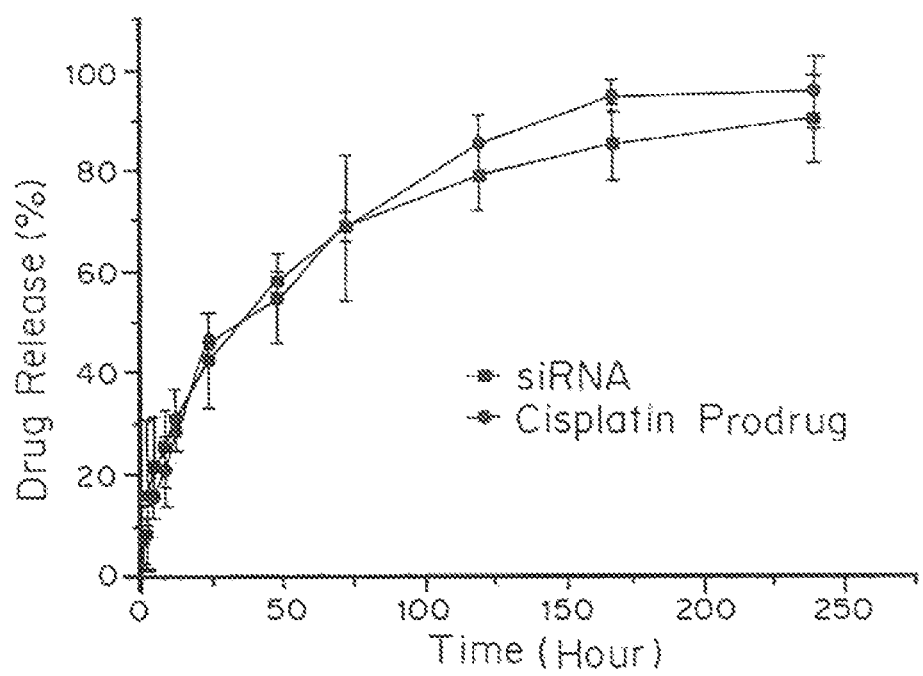
FIG. 2 is a graph showing the in vitro release profile of the siRNA and compound 1 from PLGA-b-PEG/G0-C14 NPs (percent drug release) as a function of time (hours).

As shown in FIG. 2, 15.7% of the total platinum compound was rapidly released over the first 4 hours followed by a sustained release after 8 hours. This controlled release of Pt(IV) from the NPs extended over 1 week, reaching a maximum value of 95% thereafter. The release profile of Cy3-labeled siRNA was measured using fluorescent spectrophotometry, which showed that 50% of the total siRNA was released at 30 hours and reached a maximum value of 91% over 10 days. The above results demonstrate that NPs enable the dense loading and sustained release of a combination payload of siRNA and chemotherapeutic drugs.

Example 5

Platinum Uptake Evaluation

Materials and Methods

The cellular uptake of NP(Compound 1) and free Compound 1 was studied using a LNCaP cell line. LnCaP cells were seeded into 6-well plates (2.5×10$^6$ cells/well) and allowed to adhere overnight in growth medium. NP(Compound 1) and free Compound 1 were added to the growth media at a final platinum concentration of 0.1 mM. Six hours after nanoparticle incubation, the cells were washed with PBS buffer, followed by treatment with nitric acid for 3 hours. The cell lysate was collected and the cellular platinum concentration was quantitatively determined by AAS. The platinum content was normalized against protein concentration in the cell extracts, measured by a BCA protein kit. Data were reported as mean standard deviation for triplicate samples and the experiment was repeated twice.

Results

Figure 10:
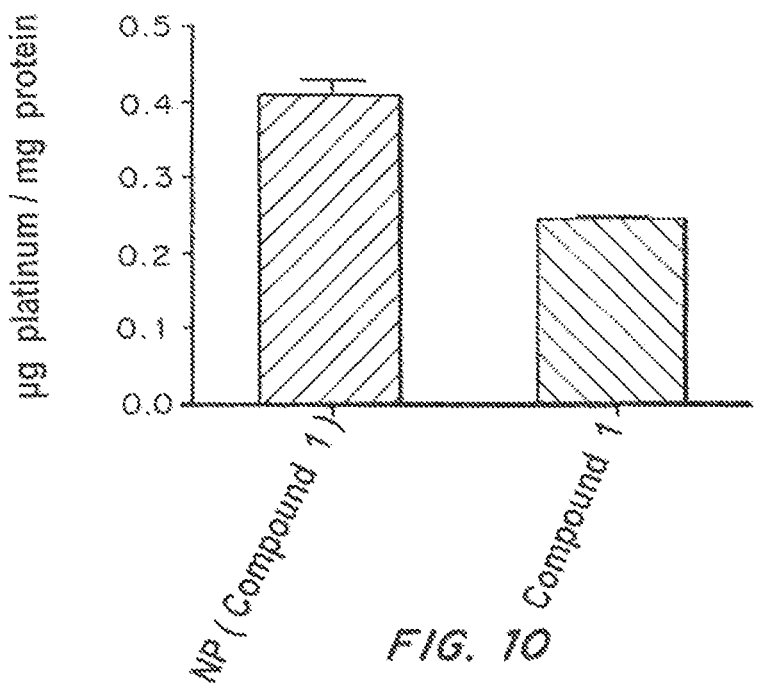
FIG. 10 is a graph shows the AAS analysis of platinum content within LNCaP cells treated with an equivalent dose of compound 1 either in solution or NP form.

As shown in FIG. 10, cells treated with NP (compound 1) had taken up around 50% more platinum compared to cells treated with free compound 1. The enhanced cellular uptake of platinum is probably a consequence of the improved solubility of compound 1 in aqueous systems when encapsulated within NPs. Another possible explanation is that NPs shield compound 1 from unspecific interactions with albumin present in the cell growth medium, which are considered to be the main route for platinum binding in human blood plasma.

Example 6

In Vitro siRNA Transfection

Materials and Methods

Dual-Luc HeLa cells were seeded into 96-well plates (15,000 cells/well) and allowed to attach in growth medium at 37° C. in a 5% $CO_2$ incubator overnight. Cells were then transfected with naked siLuc, NPs encapsulating siLuc (NP (siLuc)), blank NP, and Lipofectamine 2000 (Lipo2000) complexed siLuc. Lipo2000 and siRNA were mixed to form lipoplex according to the manufacturer's protocol as a positive control. After 24 hours, the cells were washed with fresh medium and further incubated in the medium for one day. The expression of firefly and Renilla luciferase in HcLa cells was determined by Dual-Glo™ Luciferase assay kits (Promega). The luminescence intensity was measured using microplate reader (Tecan). All of the in vitro transfection experiments were performed in quadruplicate.

REV1/REV3L siRNA transfection of LNCaP and MDA-MB-231 cells was conducted in 6-well plates (400,000 cells/well). The cells were allowed to adhere overnight in growth medium and then were transfected with NP(siREV1, siREV3L). 24 hours post-transfection, the cells were washed with fresh medium and the cellular levels of REV1 and REV3L mRNAs were assessed at three consecutive days using qRT-PCR. In brief, the total RNA from transfected cells was extracted using the RNeasy mini-kits (Qiagen, Germantown, Md.) according to the manufacturer's protocol. qRT-PCR assays were performed using SYBR green on a BioRad thermal cycler. Primer sequences used in qPCR are: human housekeeping gene GAPDH (glyceraldehyde 3-phosphate dehydrogenase):

```
                                      (SEQ ID NO: 9)
CAATGACCCCTTCATTGACC
and human REV1:
                                      (SEQ ID NO: 10)
GACAAGCTTCCCGTTCTCAG;

(SEQ ID NO: 11)
TTGTGATGAAGCGCTGGTAG
and human REV3L:
                                      (SEQ ID NO: 12)
AGAGGCAGCACATTTCGTCT;

(SEQ ID NO: 13)
TTTGTGCCAGCAACAGAAAG
and (SEQ ID NO: 14)
CTGGGATCCATCGCTGTAGT.
```

Relative gene expression values were determined by the ΔΔCT method using StepOne Software (Applied Biosystems). Data are presented as the fold difference in target gene expression normalized to GAPDH as the endogenous reference, and relative to the untreated control cells.

NPs containing various doses of anti-firefly luciferase siRNA (siLuc) were incubated with cells in the presence of growth media and the expression of both reporter proteins was measured one day post-transfection. In this assay, reduction in firefly luciferase expression in the absence of Renilla reduction was considered to be the consequence of siRNA-mediated silencing. Renilla expression was monitored as an internal control for nanocarrier-associated toxicity. The gene knockdown efficacy of NPs(siLuc) was determined by the comparison of detected protein expression levels in treated groups against the untreated control and expressed as relative firefly luciferase expression.

Results

Figure 3A:
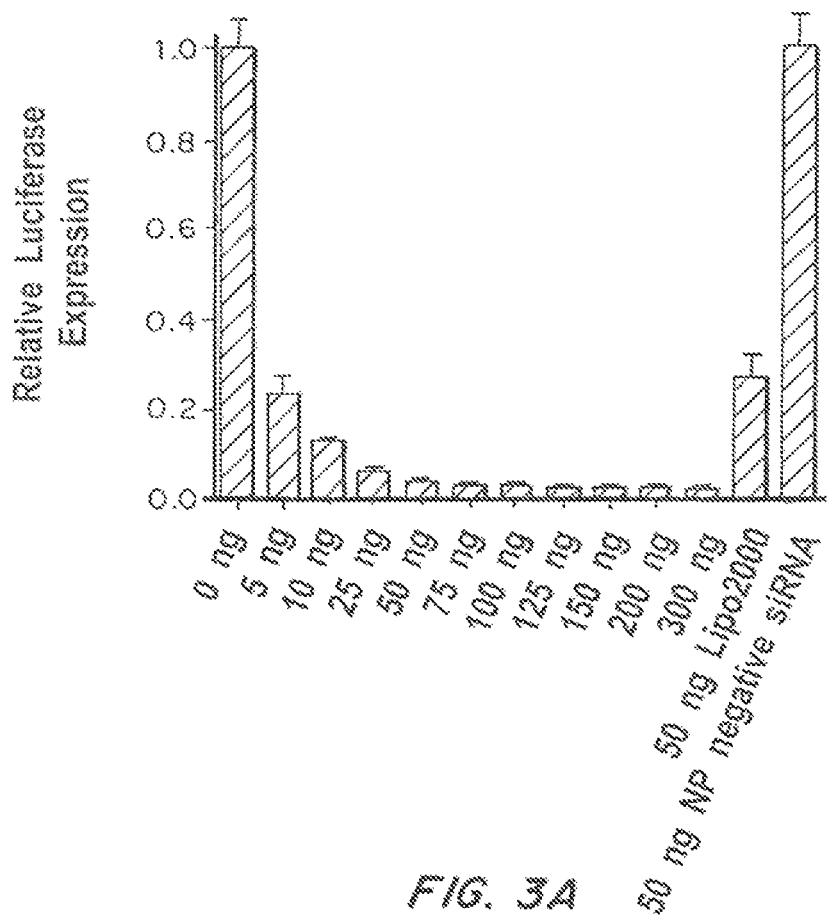
FIG. 3A is a graph showing the relative firefly luciferase expression of Dual-Luc HeLa cells transfected with NP(siLuc) at escalating dose of siLuc. Relative firefly luciferase expression was determined by comparison of detected protein levels in treated groups vs. untreated control. Lipo2000-siRNA complex containing 50 ng siRNA was used as a positive control.
Figure 3B:
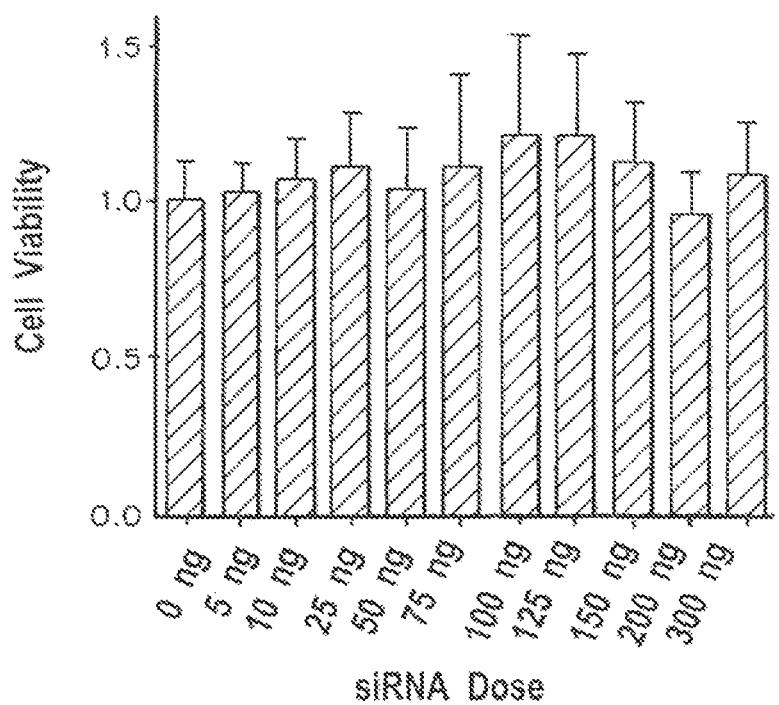
FIG. 3B is a graph showing the viability of Dual-Luc HeLa cells incubated with escalating dose of NP(siLuc).

The performance of the NPs is plotted as a function of siRNA dose as shown in FIG. 3A. NP that lacked siRNA (blank NP) produced no silencing effects while luciferase expression was significantly silenced with an increase of siLuc dose in NPs. When a dose of siRNA at or above 25 nanograms (ng) was used, NP(siLuc) achieved greater than 95% luciferase knockdown, a more efficient silencing efficacy than the commercially available liposome-based lipoplex (Lipo2000-siRNA complex). It should also be noted that no evidence of cellular toxicity was observed by the XTT (2,3-Bis-(2-Methoxy-4-Nitro-5-Sulfophenyl)-2H-Tetrazolium-5-Carboxanilide) assay under all the conditions used for in vitro transfection experiments (FIG. 3B).

Example 7

In Vitro Viability Assays

Materials and Methods

To examine the cytotoxicity of the siRNA-containing NPs, Dual-Luc cells were seeded in quadruplicate in 96-well plates (15,000 cells/well). The cells were allowed to adhere overnight in growth medium and then treated with formulations containing escalating-dose of NP(siLuc). Cells in media containing 10% FBS with nothing added were used as controls. 24 hours after treatment, cell viability was measured using XTT assay (Roche Applied Science, Indianapolis, Ind.) following the manufacturer's protocol. To investigate the dose response of the siRNA-containing formulations, the LNCaP cells were first transfected with NP(siREV1, siREV3L) for 24 h and the medium was replaced with fresh medium thereafter. The cells for were incubated another 24 hours, after which the transfected cells were seeded in quadruplicate in 96-well plates (15,000 cells/well) and treated with two different formulations with escalating-dose of compound 1. The first formulation consists of NP(siREV1,siREV3L) with compound 1 in solution form and the second contains compound 1 within the NP [NP(siREV1, siREV3L, compound 1)]. Untransfected cells were seeded and treated with escalating-dose of compound 1 either in solution or NP form. Cell viability was then measured using XTT assay 24 hours post treatment.

Results

Figure 7:
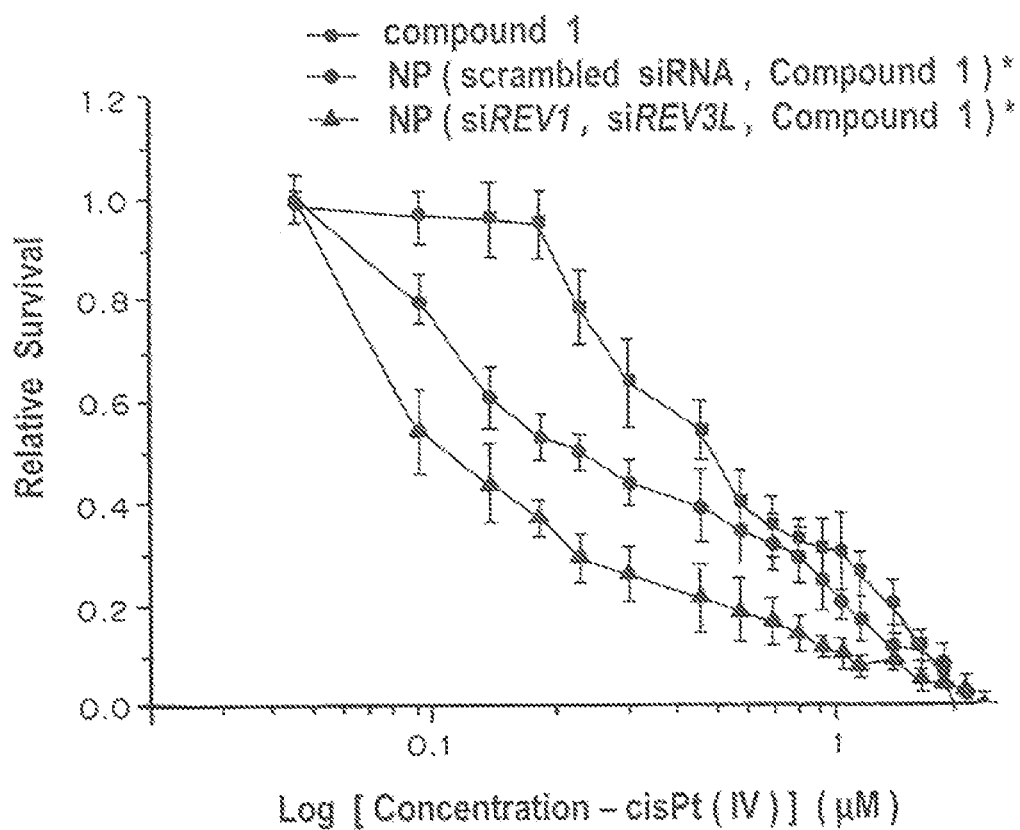
FIG. 7 is a graph showing platinum dose-response curves of LNCaP cells treated with free Compound 1 (squares), NP(scrambled siRNA, compound 1) (circles) and NP(siREV1, siREV3L, compound 1) (triangles). The experiment was conducted in quadruplicate (n=4). *Prior to treatment with the two siRNA-containing NP formulations, the cells were transfected with NP(siREV1, siREV3L) or NP (scrambled siRNA) for 48 hours.

The cells treated with NP(siREV1, siREV3L) exhibited better dose-response to free drug than the untreated cells, providing evidence for the enhanced chemosensitization of prostate cancer cells through REV1 and REV3L suppression. Similarly, inclusion of the REV1/REV3L siRNAs in NPs resulted in improved tumor cell response to compound 1-loaded NPs compared to NP (scrambled siRNA, compound 1) (FIG. 7). It is important to recognize that the lowest EC50 value was attributed to the NP formulation loaded with both siRNA and compound 1. Taken together, these results indicate that the simultaneous delivery of siRNAs and compound 1 is able to concurrently knockdown expression levels of genes REV1 and REV3L and sensitize cultured cancer cells to platinum treatment. These findings are consistent with previous studies, which have revealed that cells lacking either Rev1 or Rev3L displayed a reduced drug-induced mutation in response to DNA-damaging agents and an increased sensitivity to DNA damaging chemotherapy.

Example 8

In Vivo Bioluminescence Imaging

Materials and Methods

Luciferase-expressing xenograft tumors were induced in the mammary fat pad of 8-week-old BALB/C nude mice (Charles River Laboratories International, Inc. Wilmington, Mass.) by subcutaneous (s.c.) injection of $1 \times 10^6$ luciferase-expressing MDA-MB-231 cells suspended in 1:1 media and matrigel. After two weeks, NP(siLuc) and NP(negative siRNA) were administrated into the tumor-bearing nude mice (tumor size~100-150 mm$^3$) Tumor length and width were measured with calipers, and the tumor volume was calculated using the following equation: tumor volume (V)=length×width×width/2. The NP solution was concentrated to 15 mg/mL with the total encapsulated siRNA concentration being ~150 µg/mL. The siRNA-containing NPs were directly injected into the tumor at an equivalent dose of ~0.4 mg/kg entrapped siRNA. Right before dosing, the mice were monitored using an IVIS Spectrum bioluminescent and fluorescent imaging system (Caliper Life Sciences). Tumor bioluminescence images were then taken daily for 3 days post-injection. The bioluminescence intensity was analyzed using LivingImage acquisition and analysis software. All of the in vivo imaging experiments were performed in quintuplicate.

Luciferase-expressing MDA-MB-231 cells were subcutaneously injected to the mammary fat pad of nude mice to develop xenograft tumors that stably express luciferase. Two weeks post tumor xenograft the gene knockdown efficacy experiments were initiated. Ten tumor-bearing nude mice were randomly divided into two groups (n=5), with each group administered either NP(negative siRNA) (control group) or NP(siLuc) (experiment group) through a single intratumoral injection. The initial bioluminescence images of the mice were obtained (day 0), after which the mice were injected with a single dose of NP(siLuc). The treated mice were then imaged thereafter for 3 consecutive days.

Results

The bioluminescence intensity from the control group mice increased rapidly from day 0 to day 3 with day 3 being a near 64% increase in intensity compared to day 0. In contrast, the tumors treated with NP(siLuc) showed a drastic decrease in bioluminescence intensity one-day post injection and increased in the following days. These results suggest that the NPs are capable of delivering siRNA to inhibit luciferase expression in vivo.

Figure 4:
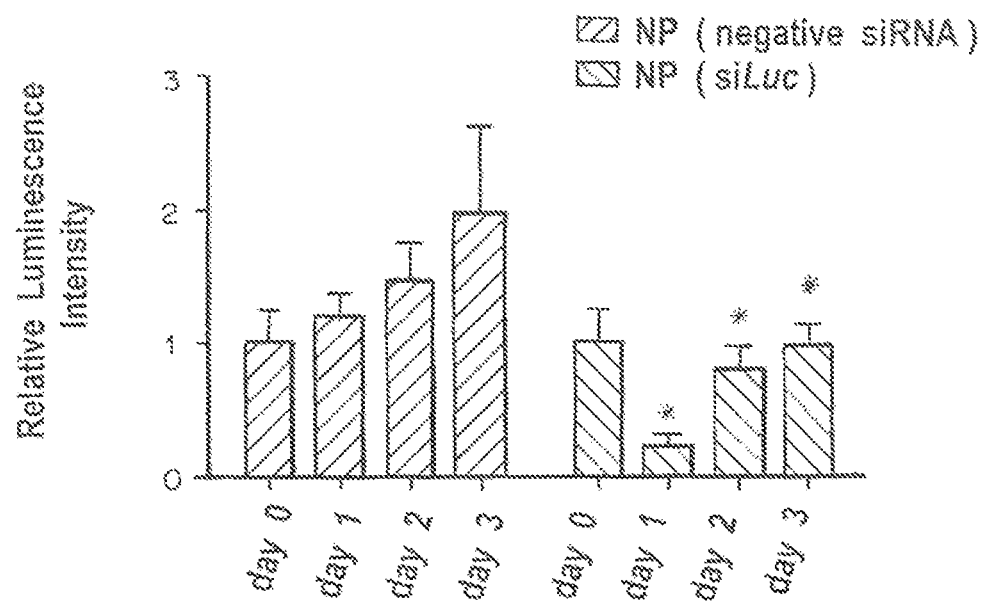
FIG. 4 is a graph showing in vivo bioluminescence imaging. Luciferase-expressing xenograft tumors were induced in the mammary fat pad of 8-week-old BALB/C nude mice (Charles River Laboratories International, Inc. Wilmington, Mass.) by subcutaneous (s.c.) injection of $1\times10^6$ luciferase-expressing MDA-MB-231 cells suspended in 1:1 media and matrigel. After two weeks, NP(siLuc) and NP(negative siRNA) were administrated into the tumor-bearing nude mice (tumor size~100-150 mm$^3$) Tumor length and width were measured with calipers, and the tumor volume was calculated using the following equation: tumor volume (V)=length×width×width/2. The NP solution was concentrated to 15 mg/mL with the total encapsulated siRNA concentration being approximately 150 μg/mL. The siRNA-containing NPs were directly injected into the tumor at an equivalent dose of approximately 0.4 mg/kg entrapped siRNA. Right before dosing, the mice were monitored using an IVIS Spectrum bioluminescent and fluorescent imaging system (Caliper Life Sciences). Tumor bioluminescence images were then taken daily for 3 days post-injection. The bioluminescence intensity was analyzed using LivingImage acquisition and analysis software. All of the in vivo imaging experiments were performed in quintuplicate.

In order to quantify the gene silencing efficacy of NP(siLuc), the bioluminescence intensity signals obtained for each tumor at different days were normalized by setting the initial bioluminescent signal (day 0) equal to 1. The relative luminescence intensity (n=5, mean±SE) was then plotted as a function of time (FIG. 4). An 80% decrease in luciferase expression in the treated group was observed one day post injection. Furthermore, the bioluminescence intensity of days 2 and 3 relative to day 0 remains a fractional part (71.4% and 85.7%, respectively), indicating a sustained gene silencing effect. These results are consistent with the in vitro data. NP(siLuc) exhibited a remarkable in vivo efficacy in suppressing luciferase expression in the MDA-MB-231 cells.

Example 9

In Vivo Gene Silencing of REV1 and REV3L

Materials and Methods

LNCaP cells were first retrovirally infected to stably express GFP protein. Retroviral vector used is well known MSCV/LTRmiR30-SV40-GFP which is under control of the SV40 promoter. MSCV vector was transfected into 293T cell line by Calcium method to produce retro virus. Following incubation with retro virus, LNCaP cells were sorted on MoFlo flow cytometer. The GFP-labeled LNCaP cells ($10^6$ cells, 0.1 mL) were injected subcutaneously into the flank of a male SCID-beige mouse using 50% matrigel. Tumor nodules were allowed to grow to a volume of approximately 100 mm$^3$ prior to treatment. Tumor-bearing mice were randomly assigned to two groups (n=4) to minimize weight and tumor size differences among the groups. Each group was administered with either NP (negative siRNA) (control group) or NP (NP(siREV1, siREV3L) at a dose of 0.4 mg siRNA per kg animal via intratumoral injection. After euthanasia, the tumor tissues were dissected from the mice at the designated time points and pure populations of live LNCaP cells were isolated by GFP sorting. The cellular expression levels of siREV1 and siREV3L mRNAs from the sorted cells were assessed using qRT-PCR as described above.

Results

Figure 9A:
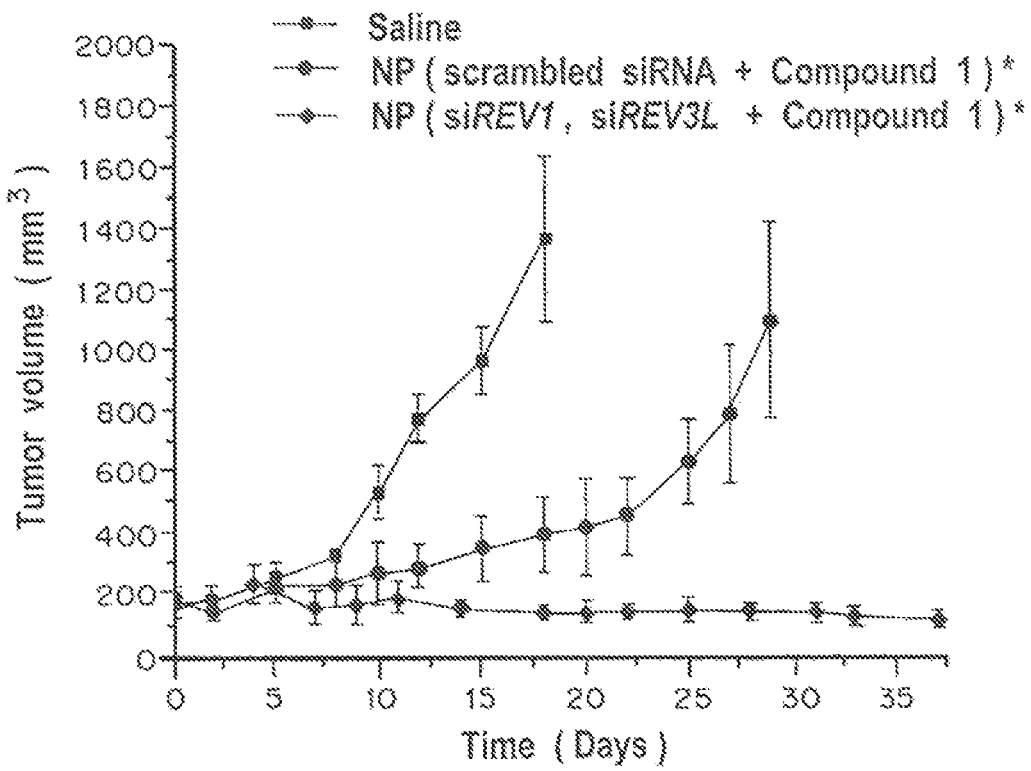
FIG. 9 is a graph showing inhibition of LNCaP xenograft tumor growth by (iii) NP(siREV1, siRE V3L, compound 1) in comparison with (i) saline and (ii) NP(scrambled siRNA, compound 1). The dose of compound 1 and siRNA per injection was 4 mg/kg and 0.4 mg/kg, respectively.
FIG. 9B is a graph showing survival curves of tumor-bearing mice treated with the aforementioned 3 formulations. Day 0 represents the first day of NP(siREV1, siREV3L) or NP(scrambled siRNA) administration. [n=5 for group (i) and (ii), n=8 for group (iii)] P<0.003 NP(scrambled siRNA, compound 1) vs NP(siREV1, siRE V3L, compound 1). P values for all survival studies were determined using log-rank curve comparison tests. *Prior to treatment with the two siRNA-containing NP formulations, the tumor-bearing mice were injected on day 0 and day 2 with NP(siREV1, siREV3L) or NP(scrambled siRNA). Starting from the 4th day, the mice received intratumoral injections of the aforementioned 3 formulations twice weekly.
Figure 9B:
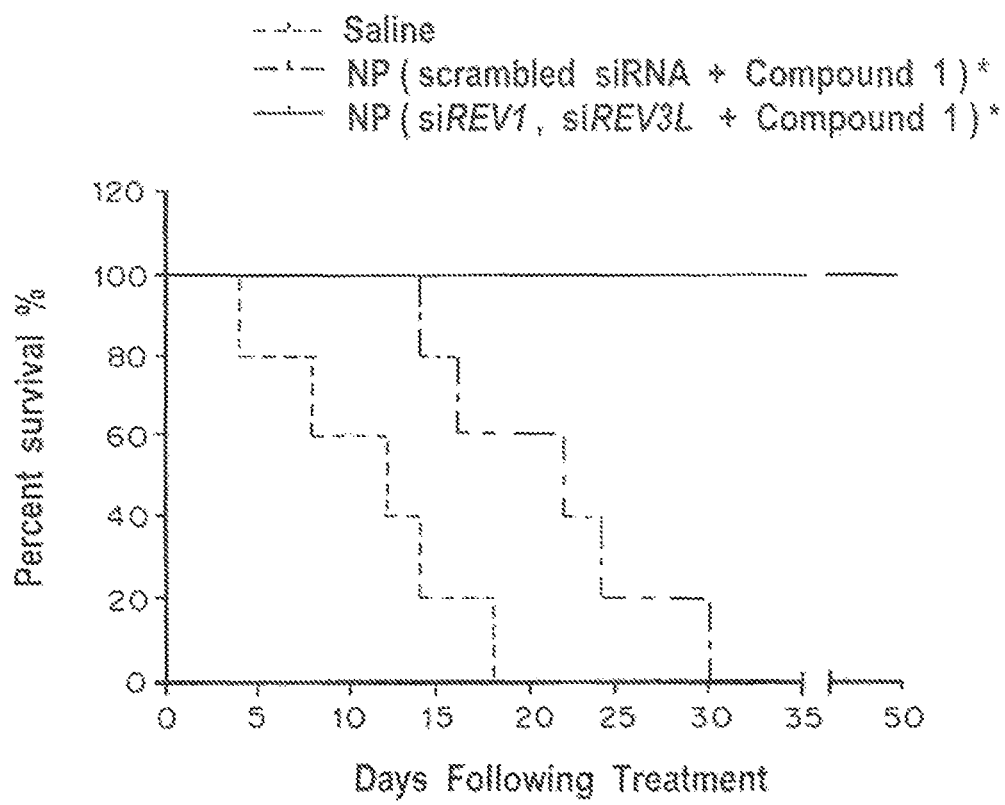

The results are shown in FIGS. 9A and 9B. Efficacy of the combined siRNA and compound 1 in the NPs was striking.

Example 10

In Vivo Anticancer Efficacy Evaluation

Materials and Methods

The mouse LNCaP xenograft tumor model was developed by injecting 0.1 mL LNCaP cell suspension ($10^6$ cells) into the flank of a male SCID-beige mouse using 50% matrigel. Tumor nodules were allowed to grow to a volume of approximately 100 mm$^3$ before initiating treatment. Tumor-bearing mice were randomly assigned to five groups prior to treatment, and their weight and the initial tumor volume were measured and recorded, respectively. Starting from day 4, test animals received two intratumoral injections weekly at intervals of 3 or 4 d of (i) saline, (ii) compound 1 in solution form, (iii) compound 1 encapsulated NP (NP(compound 1)), (iv) NP(siREV1, siREV3L) with compound 1 in solution, and (v) NP(siREV1, siREV3L, compound 1) formulations for 34 days (n=5 for group (i)-(iv), n=8 for group (v)). It should be noted that prior to treatment with the two siRNA-containing NP formulations (regimens (iv) and (v)), the mice were injected with NP(siREV1, siREV3L) on day 0 and day 2 at an equivalent dose of ~0.4 mg/kg entrapped siRNA in order for REV1/REV3L depletion to occur at noticeable levels. At day 4, injections were initiated with the aforementioned 5 formulations at an equivalent dose of 4 mg/kg for compound 1 and 0.4 mg/kg for siRNA per injection. The weight and tumor volume of each mouse were measured twice weekly over a period of 37 days.

Several classes of cancer drugs, including platinum-based compounds and cyclophosphamide, attack cancer cells by damaging their DNA. This DNA damage can prevent cells from replicating their DNA before dividing, which usually induces apoptosis. However, cancer cells can use enzymes known as translesion DNA polymerases to carry out TLS, allowing them to escape apoptosis. This type of DNA replication is highly prone to errors, thereby introducing mutations into the DNA. These newly acquired mutations can allow cancer cells that survive chemotherapy to be much more drug-resistant and aggressive. Thus error-prone TLS can induce massive genomic mutations after DNA-damaging chemotherapy while also helping the cells avoid the cytotoxic effect of the treatment.

In human cells, several gene products are major contributors to drug-induced mutagenesis. For example, Rev1 is a scaffolding protein that recruits other translesion DNA polymerases to DNA lesions. It is also a dCMP transferase that contributes to the bypass of certain lesions. Rev3L is the catalytic subunit of DNA polymerase ζ (Pol ζ), which plays a key role in extending replication termini across DNA damage. It has been found that human cells expressing reduced levels of genes REV1 and REV3L are more sensitive to cytotoxicity by cisplatin. Thus, it was hypothesized that the suppression of REV1 and REV3L by specific siRNA-containing NPs would inhibit TLS activity, impair drug-induced mutagenesis, and consequently sensitize cancer cells to chemotherapy.

Using human prostate cancer LNCaP cells and breast cancer MDA-MB-231 cells as two cell models, the knockdown efficiency of these target genes by NP(siREV1, siREV3L) was determined After 24 hours incubation with NPs, the cells were washed with fresh medium and the cellular levels of REV1 and REV3L mRNA were assessed on three consecutive days using quantitative real-time PCR (qRT-PCR).

Results

Figure 5A:
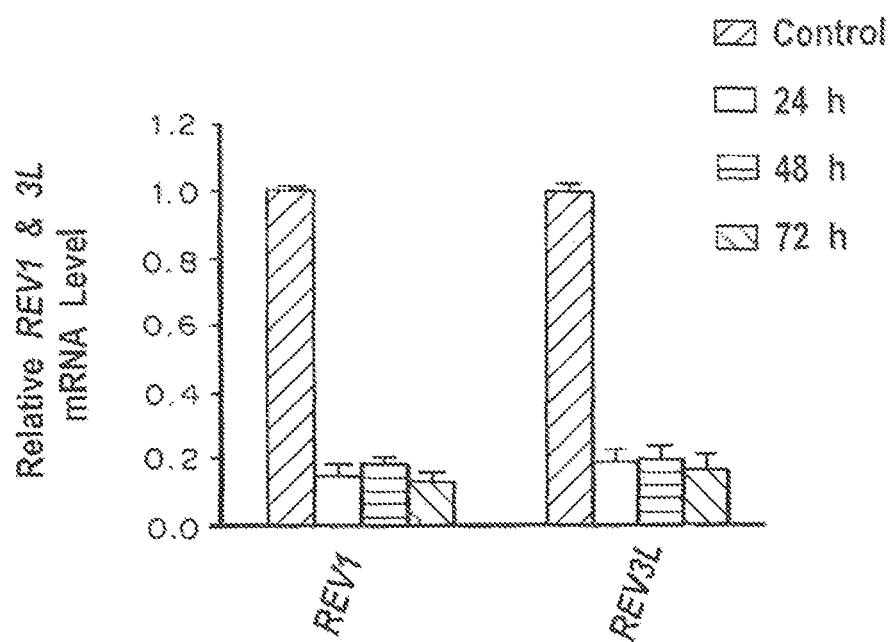
FIG. 5A is a graph showing qRT-PCR confirmation of REV1 and REV3L gene suppression using NP(siRE V1, siREV3L) in LNCaP human prostate adenocarcinoma cells at 24, 48 and 72 hr.
Figure 5B:
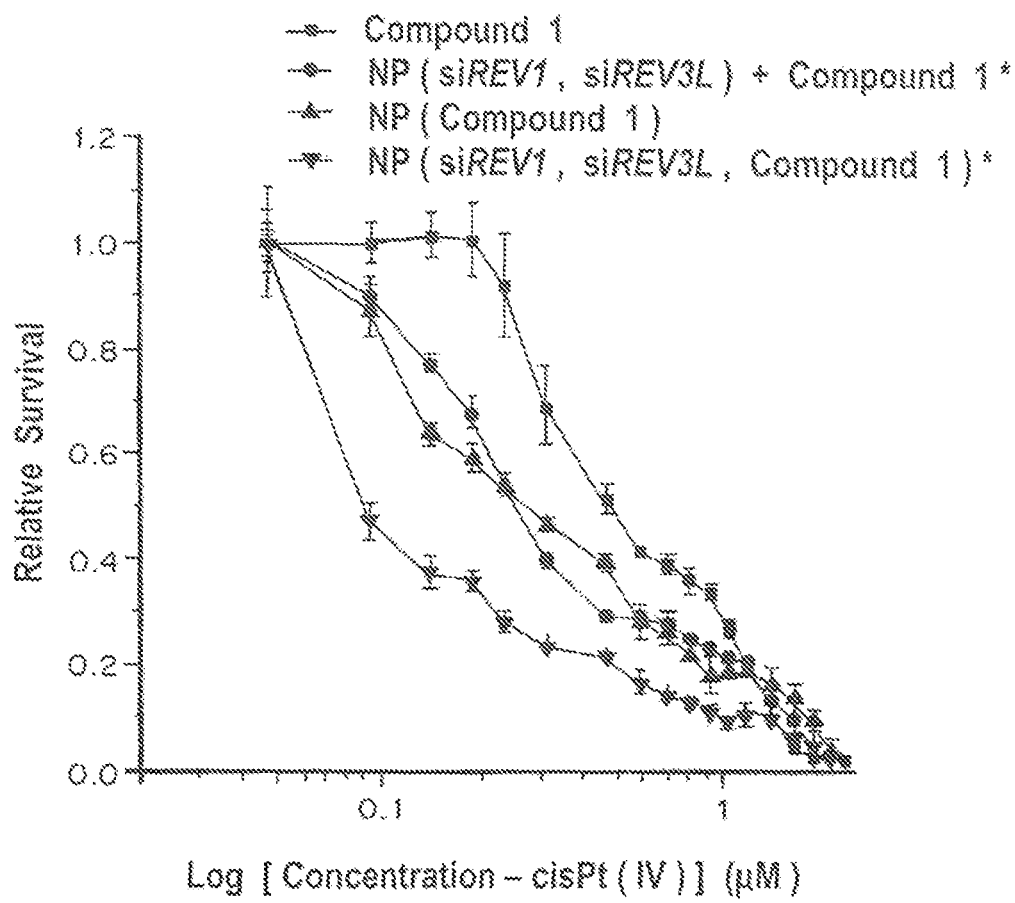
FIG. 5B is a graph showing platinum dose-response curves (relative survival) in cells expressing normal [compound 1 in solution form, NP(compound 1)] or impaired [NP(siREV1, siREV3L) with compound 1 in solution form, NP(siREV1, siREV3L, compound 1)] levels of REV1 and REV3L. The experiment was conducted in quadruplicate (n=4). *Prior to treatment with the two siRNA-containing NP formulations, the cells were transfected with NP(siREV1, siREV3L) for 48 hours. The transfected cells were then treated with the two different formulations with escalating-dose of compound 1.
Figure 6:
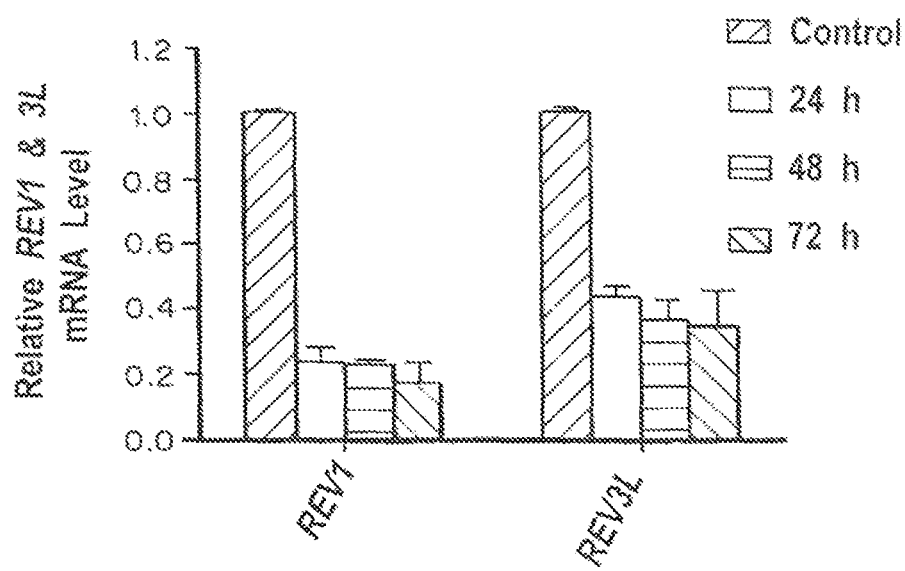
FIG. 6 is a graph showing qRT-PCR confirmation of REV1 and REV3L gene suppression using NP(siREV1, siREV3L) in MDA-MB-231 human breast carcinoma cells at 24, 48 and 72 hr.

As shown in FIG. 5A, the qRT-PCR assay revealed a sustained knockdown efficiency of up to 87% for both genes REV1 and REV3L in LNCaP cells over the course of three days. A similar gene silencing efficacy was observed in MDA-MB-231 cells (FIG. 6). Notably, these developed NPs are capable of simultaneously targeting multiple genes. An escalating-dose experiment in LNCaP cells was done to examine the effects of NP-mediated REV1/REV3L suppression on tumor cell chemosensitivity. The following four different formulations were compared: (i) compound 1 in solution form, (ii) compound 1 encapsulated NP [NP(compound 1)], (iii) NP(siREV1, siREV3L) with compound 1 in solution, and (iv) NP(siREV1, siREV3L, compound 1). Prior to treatment with the two siRNA-containing NP formulations, the cells were transfected with NP(siREV1, siREV3L) for 24 hours in order to achieve substantial levels of Rev 1 and Rev3L suppression. The transfected cells were then treated with the two different siRNA-containing formulations with escalating-dose of compound 1. The first formulation consists of NP(siREV1, siREV3L) with compound 1 in solution form, whereas the second contains compound 1 within the NP [NP(siREV1, siREV3L, compound 1)]. A comparison of the dose-response curves revealed significantly lower EC50 values for all three NP formulations when compared to free drug in solution form (FIG. 5B). As expected, the cells treated with NP(siREV1, siREV3L) exhibited better dose-response to free drug than the untreated cells, thus providing evidence for the enhanced chemosensitization of prostate cancer cells through REV1 and REV3L suppression. Similarly, inclusion of the REV1/REV3L siRNAs in NPs resulted in improved tumor cell response to compound 1-loaded NPs compared to NP(scrambled siRNA, compound 1) (FIG. 7). It is important to recognize that the lowest $EC_{50}$ value was attributed to the NP formulation loaded with both siRNA and compound 1, suggesting a greater potency and efficacy compared to the other therapeutic formulations. It was discovered that whether the compound 1 is delivered free or within NPs plays a crucial role in cell survival. In order to investigate how encapsulation of 1 affects cell survival rates, LNCaP cells were incubated with an equivalent dose of the compound either in solution or NP form, and the platinum content of the cell was determined by AAS. As shown in FIG. 10, cells treated with NP (compound 1) had taken up around 50% more platinum compared to cells treated with free compound 1. The enhanced cellular uptake of platinum is probably a consequence of the improved solubility of compound 1 in aqueous systems when encapsulated within NPs. Another possible explanation is that NPs shield compound 1 from unspecific interactions with albumin present in the cell growth medium, which are considered to be the main route for platinum binding in human blood plasma. Taken together, these results indicate that the simultaneous delivery of siRNAs and compound 1 is able to concurrently knockdown expression levels of genes REV1 and REV3L and sensitize cultured cancer cells to platinum treatment. These findings are consistent with previous studies, which have revealed that cells lacking either Rev1 or Rev3L displayed a reduced drug-induced mutation in response to DNA-damaging agents and an increased sensitivity to DNA damaging chemotherapy.

Example 11

In Vivo Anticancer Efficacy Evaluation

Materials and Methods

Using a well-established LNCaP xenograft mouse model of prostate cancer, it was investigated whether PLGA-b-PEG/G0-C14 hybrid NPs are capable of inhibiting REV1 and REV3L expression in tumors. LNCaP cells were first retrovirally infected to stably express green fluorescent protein (GFP) before they were injected into SCID-beige mice to develop xenograft tumors. In this study, GFP was used as a marker for implanted LNCaP cells. After the tumors reached a sufficient size of approximately 100-200 mm3, the animals were randomly divided animals into two groups (n=4) to minimize weight and tumor size differences among the groups. Each group was administered either NP (negative siRNA) (control group) or NP(siREV1, siREV3L) (experimental group) at a dose of 0.4 mg siRNA per kg animal via intratumoral injection. Tumors were harvested from the mice at the designated time points and pure populations of LNCaP cells were isolated by GFP sorting before qRT-PCR.

The efficacy of injecting nanoparticles that contained both the Pt(IV) prodrug and the siRNAs directed against REV1 and REV3L [NP(siREV1, siREV3L, compound 1)] using the LNCaP xenograft mouse model as described above was also investigated. Three weeks after inoculation with LNCaP cells, mice were randomly divided into 5 groups and treated with the following regimens with equivalent doses of compound 1 via intratumoral administration twice weekly for 5 weeks: (i) saline, (ii) compound 1 in solution form, (iii) compound 1 encapsulated NP [NP(compound 1)], (iv)

NP(siREV1, siREV3L) with compound 1 in solution, and (v) NP(siREV1, siREV3L, compound 1). It should be noted that prior to treatment with the two siRNA-containing NP formulations [regimens (iv) and (v)], mice were injected on day 0 and day 2 with NP(siREV1, siREV3L) to ensure that Rev1 and Rev3L depletion occurred at significant levels. At day 4, injections with the aforementioned 5 formulations were initiated. The aim of this study was to determine whether simultaneous delivery of REV1/REV3L specific siRNAs and platinum chemotherapeutics would result in enhanced antitumor activity through synergistic effects.

Results

Figure 8A:
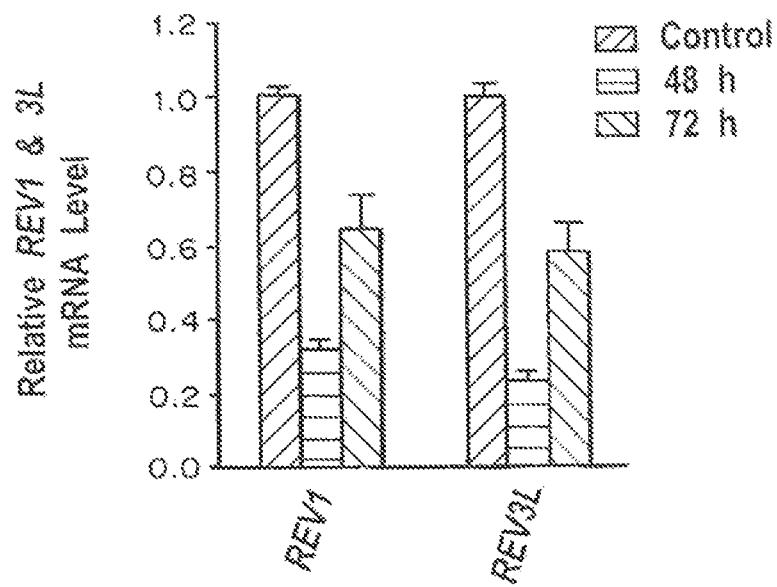
FIG. 8A is a graph showing qRT-PCR confirmation of REV1 and REV3L gene suppression in LNCaP cells that were harvested from xenograft tumor and isolated by GFP sorting 2 or 3 days post injection of NP(siREV1, siREV3L).

FIG. 8A showed that the cellular levels of REV1 and REV3L expression were significantly decreased by 78% relative to the control in the harvested GFP-labeled LNCaP cells 48 hours post-treatment. Additionally, the gene silencing effect mediated by a single dose of NP(siREV1, siREV3L) was still noticeable 72 hours after administration (36% and 42% decrease in REV1 and REV3L, respectively). In this context, these results further demonstrate that the NPs are able to efficiently deplete REV1 and REV3L expression in tumors.

Figure 8B:
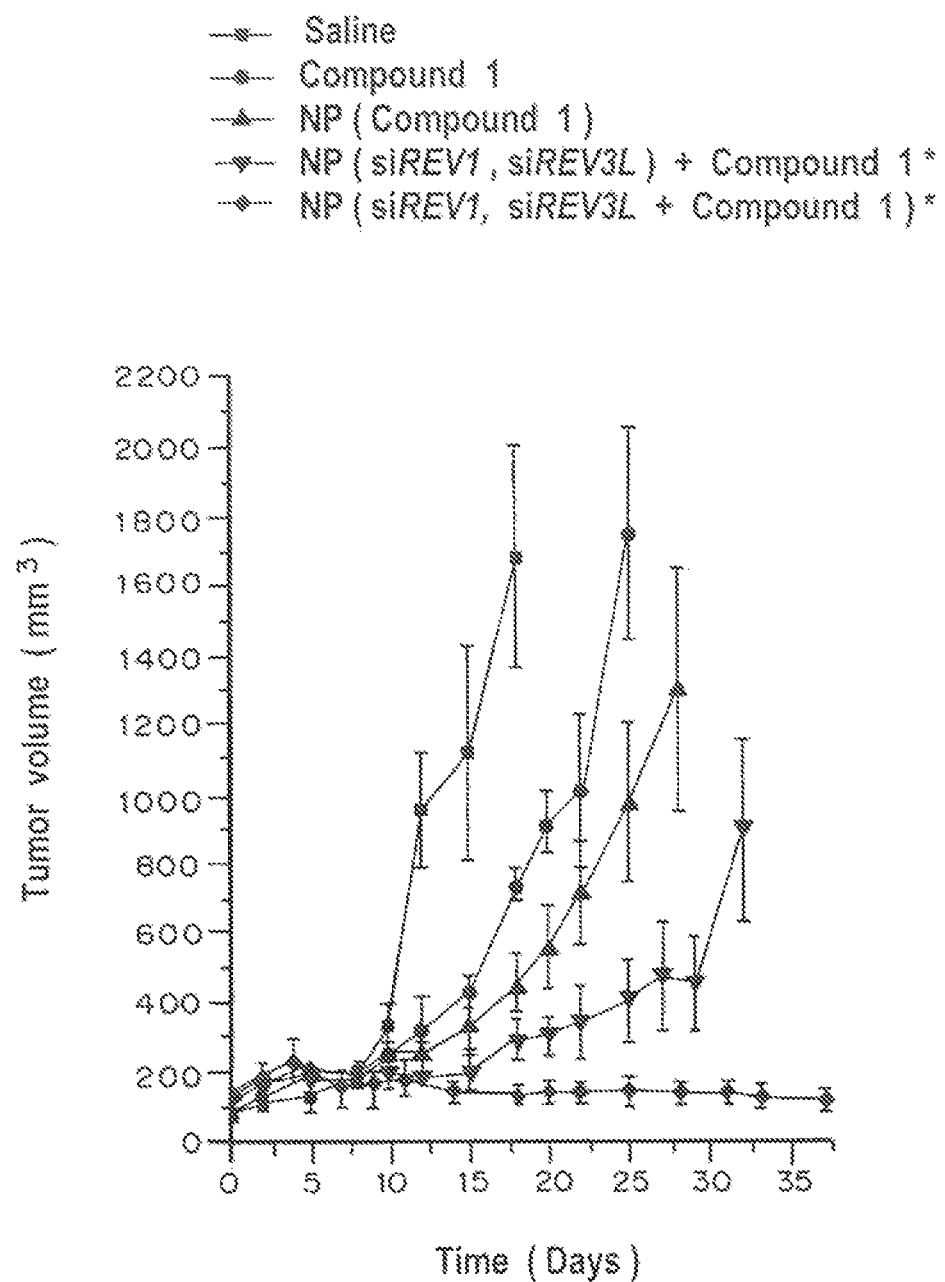
FIG. 8B is a graph showing the inhibition of LNCaP xenograft tumor growth by (v) NP(siREV1, siREV3L, compound 1) in comparison with the following formulations: (i) saline, (ii) compound 1 in solution form, (iii) compound 1 encapsulated NP [NP(compound 1)], and (iv) NP(siREV1, siREV3L) with compound 1 in solution. The dose of compound 1 and siRNA per injection was 4 mg/kg and 0.4 mg/kg, respectively.
Figure 8C:
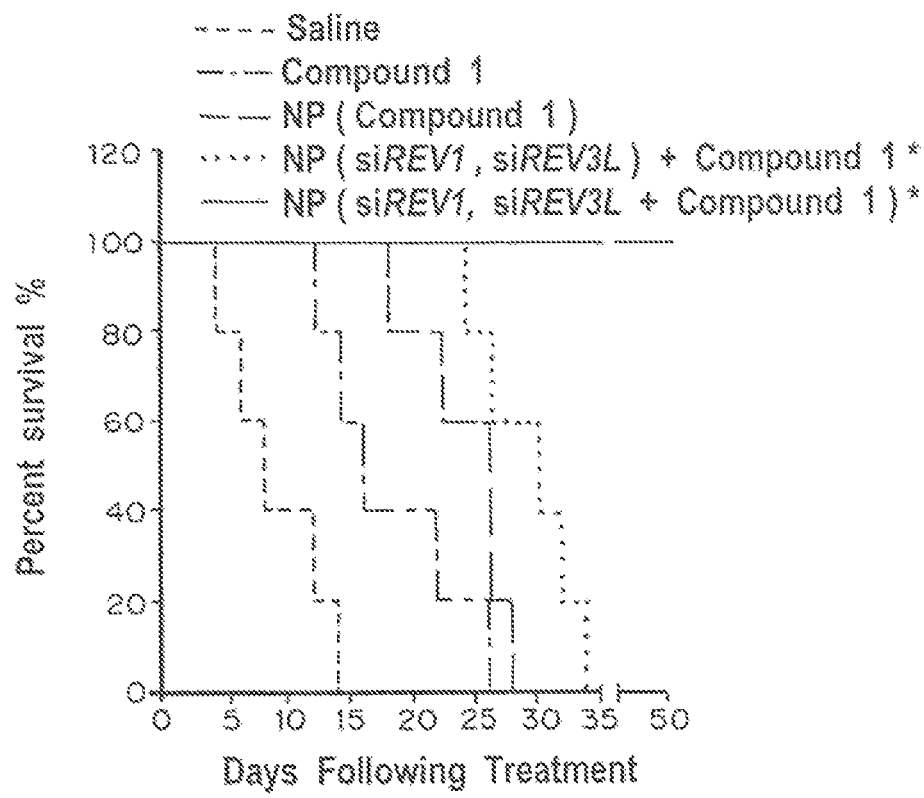
FIG. 8C is a graph showing the survival curves of tumor-bearing mice treated with the aforementioned 5 formulations. Day 0 represents the first day of NP(siREV1, siREV3L) administration. [n=5 for group (i)-(iv), n=8 for group (v)] P<0.0136 Compound 1 vs NP(siREV1, siREV3L)+Compound 1; P<0.008 NP(Compound 1) vs NP(siREV1, siREV3L, compound 1). P values for all survival studies were determined using log-rank curve comparison tests. *Prior to treatment with formulations (iv) and (v), the tumor-bearing mice were injected on day 0 and day 2 with NP(siREV1, siREV3L). Starting from the 4th day, the mice received intratumoral injections of the aforementioned 5 formulations twice weekly. Day 0 represents the first day of NP(siREV1, siREV3L) administration.

From FIG. 8B, it is clear that the administration of NP(siREV1, siREV3L, compound 1) resulted in a virtually complete inhibition in tumor growth. Moreover, the tumors treated with NP(siREV1, siREV3L, compound 1) seemed to decline slightly in volume post injections. Notably, tumors treated with a combination of NP(siREV1, siREV3L) and compound 1 in solution displayed delayed growth when compared to their drug-only counterparts, again emphasizing that suppression of REV1/REV3L expression can improve the antitumor response of chemotherapy irrespective of whether 1 is delivered free or within NPs (FIG. 8B). Additionally, inclusion of the REV1/REV3L siRNAs in NPs carrying compound 1 increased their effectiveness [compare (v) to (iii) and (v) to the NP(scrambled siRNA, compound 1) group], further emphasizing that suppressing REV1/REV3L expression can enhance tumor growth suppression (FIGS. 8B and 9A). These results remain consistent with the in vitro escalating-dose experiment (FIGS. 5B and 7). Strikingly, all mice treated with NP(siREV1, siREV3L, compound 1) survived the entire 50-day study duration without tumor growth (FIG. 8C). In contrast, no other group had animals survive the 34-day study (FIGS. 8C and 9B). The combination of NP(siREV1, siREV3L) with compound 1 in solution (regimen (iv)) was also more efficacious with respect to survival than the free drug, NP(compound 1), and saline control groups, resulting in mice living a relatively healthy period of 20 days. However, regimen (iv) was less efficacious with respect to survival when compared to the NP(siREV1, siREV3L, compound 1) group. Inclusion of scrambled siRNA in compound 1-loaded NP also decreased the survival rate compared to the NP(siREV1, siREV3L, compound 1) group (FIG. 9B). This study strongly suggests that the combinational effects of siRNA targeting TLS polymerases and an anti-cancer drug in the NPs can significantly improve survival in tumor bearing mice.

We claim:

1. A nanoparticle formulation for delivery of at least two different therapeutic agents, wherein the formulation comprises nanoparticles each comprising (a) an aqueous core comprising one or more hydrophilic therapeutic nucleic acids in a loading between about 0.01 and 10% (wt/wt) of the total weight of the nanoparticles; and (b) a shell comprising one or more hydrophobic cationic moieties, one or more amphiphilic moieties comprising a biodegradable hydrophobic polymer and a hydrophilic polymer, and one or more hydrophobic small molecule therapeutic agents, wherein the hydrophobic small molecule therapeutic agent is a chemotherapeutic agent, wherein the hydrophobic cationic moieties and the biodegradable hydrophobic polymer of the amphiphilic moieties form a hydrophobic matrix, wherein the hydrophilic polymer of the amphiphilic moieties forms a corona around the hydrophobic matrix, wherein the hydrophobic small molecule therapeutic agents are homogeneously dispersed in the hydrophobic matrix in a loading between about 0.01% and 20% (wt/wt) of the total weight of the nanoparticles.

2. The formulation of claim 1, wherein the hydrophilic therapeutic nucleic acid is siRNA.

3. The formulation of claim 1, wherein the hydrophobic cationic moiety comprises a cationic small molecule, polymer, or dendrimer.

4. The formulation of claim 1, wherein the hydrophobic cationic moiety comprises polyethylenimine (PEI) functionalized with one or more hydrophobic groups.

5. The formulation of claim 1, wherein the hydrophobic cationic moiety comprises a hydrophobic group selected from the group consisting of lipophilic alkyl groups, cholesterol, and combinations thereof.

6. The formulation of claim 1, wherein the biodegradable hydrophobic polymer is poly(lactic-co-glycolic acid) (PLGA).

7. The formulation of claim 1, wherein the hydrophilic polymer is polyethylene glycol (PEG).

8. The formulation of claim 1, wherein the chemotherapeutic agent is a platinum-based chemotherapeutic agent.

9. The formulation of claim 8, wherein the platinum-based chemotherapeutic agent is selected from the group consisting of cisplatin, platinum monosuccinate, oxaliplatin, and carboplatin.

10. The formulation of claim 8, wherein the platinum-based chemotherapeutic agent is a Pt(IV) prodrug.

11. The formulation of claim 10, wherein the prodrug is cis,cis,trans-[Pt(NH$_3$)$_2$Cl$_2$(OOC(CH$_2$)$_8$CH$_3$)$_2$].

12. The formulation of claim 1, wherein the nanoparticles comprise about 10% (wt/wt) hydrophilic therapeutic nucleic acids.

13. The formulation of claim 1, wherein the mean diameter of the nanoparticles is about 200 nm.

14. A method of making the formulation of claim 1, comprising
dissolving the hydrophobic cationic moiety and the amphiphilic moiety in a water immiscible organic solvent to form a polymer solution;
adding the hydrophobic small molecule therapeutic agent to the polymer solution;
separately dissolving the hydrophilic therapeutic nucleic acid in an aqueous solution, optionally containing one or more water miscible solvents; and
adding the aqueous solution to the polymer solution to form an emulsion.

15. A method of co-delivering a hydrophilic therapeutic nucleic acid and hydrophobic small molecule therapeutic agent to a patient in need thereof, the method comprising administering an effective amount of the nanoparticle formulation of claim 1.

* * * * *